(12) United States Patent
Van Wyk et al.

(10) Patent No.: US 7,699,856 B2
(45) Date of Patent: Apr. 20, 2010

(54) METHOD, APPARATUS, AND KIT FOR THERMAL SUTURE CUTTING

(76) Inventors: Robert A. Van Wyk, 10801 Starkey Rd., #104-16, Largo, FL (US) 33777; Michael A. Rolnick, 12533 Folley Quarter Rd., Ellicott City, MD (US) 21042; Matthew P. Warden, 386 Commercial St., Apartment 4 C, Boston, MA (US) 02109; Borislav S. Simeonov, 1143 85$^{th}$ Ter. North, Apt D, St. Petersburg, FL (US) 33702-3317; Fred Baron, 7001 142$^{nd}$ Ave. North, #133, Largo, FL (US) 33771

(*) Notice: Subject to any disclaimer, the term of this patent is extended or adjusted under 35 U.S.C. 154(b) by 301 days.

(21) Appl. No.: 11/329,083

(22) Filed: Jan. 11, 2006

(65) Prior Publication Data

US 2006/0161180 A1  Jul. 20, 2006

Related U.S. Application Data

(63) Continuation-in-part of application No. 11/124,288, filed on May 9, 2005, now abandoned, which is a continuation-in-part of application No. 10/600,368, filed on Jun. 23, 2003, now Pat. No. 7,048,746.

(60) Provisional application No. 60/391,887, filed on Jun. 27, 2002.

(51) Int. Cl.
*A61B 17/10* (2006.01)

(52) U.S. Cl. .................................... 606/138

(58) Field of Classification Search ............. 606/29–31, 606/37, 39, 45, 46, 148, 167, 228; 607/96, 607/97, 98, 99
See application file for complete search history.

(56) References Cited

U.S. PATENT DOCUMENTS

| 3,234,356 A |   | 2/1966 | Babb |
|---|---|---|---|
| 4,102,341 A | * | 7/1978 | Ikuno et al. .................. 606/35 |
| 4,359,052 A |   | 11/1982 | Staub |

(Continued)

FOREIGN PATENT DOCUMENTS

WO  WO 2005/009486  2/2005

OTHER PUBLICATIONS

Extended European Search Report issued in counterpart EP application No. 06 009 231.9 on Sep. 12, 2006.

*Primary Examiner*—Todd E Manahan
*Assistant Examiner*—Michael G Mendoza
(74) *Attorney, Agent, or Firm*—Chalin A. Smith; Smith Patent Consulting, LLC

(57) ABSTRACT

A novel suture removal instrument, kit and technique are described herein. The invention utilizes a newly designed thermal filament to allow the tip of the suture removal instrument to be slipped under the stitch in order to heat and cut the stitch. Current suture removal techniques utilize scissors, forceps, and/or scalpels. These techniques, which are well known in the art, are problematic because they exert tension on the stitch and are associated with patient discomfort. Small stitches add to the difficulty of suture removal because they have less suture laxity for scissor insertion. The present invention therefore allows for more rapid suture removal with less patient discomfort and at a competitive or lower cost.

45 Claims, 28 Drawing Sheets

U.S. PATENT DOCUMENTS

| | | | |
|---|---|---|---|
| 4,384,406 A | 5/1983 | Tischlinger | 606/138 |
| 4,494,542 A | 1/1985 | Lee | 606/138 |
| 4,516,574 A | 5/1985 | Hewes, Jr. | 128/303.1 |
| 4,540,873 A | 9/1985 | Kester | 219/200 |
| 4,662,068 A | 5/1987 | Polonsky | 30/124 |
| 4,845,851 A | 7/1989 | Warthen | 30/140 |
| 5,213,097 A | 5/1993 | Zeindler | |
| 5,219,350 A * | 6/1993 | Emerson et al. | 606/107 |
| 5,452,513 A | 9/1995 | Zinnbauer et al. | 30/140 |
| 5,472,654 A | 12/1995 | Crawford | 264/163 |
| 5,565,122 A | 10/1996 | Zinnbauer et al. | 219/227 |
| 6,254,620 B1 | 7/2001 | Koh et al. | 606/167 |
| 6,726,683 B1 * | 4/2004 | Shaw | 606/31 |
| 6,733,509 B2 | 5/2004 | Nobles et al. | 606/138 |
| 2004/0002717 A1 | 1/2004 | Warden et al. | 606/138 |
| 2004/0220456 A1 | 11/2004 | Eppstein | |

* cited by examiner

METHOD, APPARATUS, AND KIT FOR THERMAL SUTURE CUTTING

PRIORITY INFORMATION

This application is a continuation-in-part of U.S. patent application Ser. No. 11/124,288, filed May 9, 2005, now abandoned, which, in turn, is a continuation-in-part of U.S. patent application Ser. No. 10/600,368 filed Jun. 23, 2003, now U.S. Pat. No. 7,048,746, which, in turn, claims the benefit of U.S. Provisional Application Ser. No. 60/391,887, filed Jun. 27, 2002. The contents of these applications are hereby incorporated by reference herein in their entirety.

TECHNICAL FIELD OF THE INVENTION

The present invention relates to the field of suture removal. More particularly, the present invention provides a method, instrument, and kit for thermally cutting a suture, which minimizes the tension placed on the suture during removal, thereby reducing pain, bleeding and tissue disruption.

BACKGROUND OF THE INVENTION

Suture removal is an important part of wound repair in medicine. Internal sutures are absorbable so they are essentially "removed" by the body. External sutures or sutures on the surface of the body are nonabsorbable. Nonabsorbable sutures are advantageous, because they have a higher tensile strength than absorbable sutures. As such, they are the preferred suture for closure of external wounds. However, they carry with them the additional task of requiring manual suture removal.

The removal of sutures is problematic for many doctors. Current suture removal techniques utilize standard instruments to manipulate and cut a stitch. This technique requires considerable tension on, and manipulation of, the stitch. The resulting pain, bleeding, and tissue disruption are uncomfortable and anxiety provoking for the patient and compromise the cosmesis of the wound repair. Lastly, the technique is time consuming for the physician.

Current manual suture removal techniques rely on two methods. The first technique utilizes a suture removal kit containing a pair of forceps, scissors, and gauze pad. This technique consists of grasping the knot of the suture with the forceps and lifting the stitch enough to slip the scissors under the suture. The scissors then cut the stitch, which is then pulled out of the skin with the forceps. Unfortunately, the scissors generally have a blunt end, making it difficult to raise the stitch sufficiently off the skin to slip the distal tip of the scissors under the stitch. Additionally, the action of bringing the scissors blades together to cut the stitch creates significant tension on the suture. The gauze, included in the suture removal kit, is most aptly used to wipe away the blood which results from the manipulation necessary to remove the suture. The second current method for suture removal replaces the scissors with a thin knife but requires the same manipulation and results in similar tissue disruption and bleeding.

It is accordingly an object of this invention to provide a method, instrument, and kit for suture removal which produces less tension in the suture than current methods.

It is accordingly a further object of this invention to provide a method, instrument, and kit for suture removal which minimizes pain, bleeding and tissue disruption.

It is a further object of this invention to provide a method, instrument, and kit for suture removal which allows sutures to be removed in less time than currently available methods and devices.

SUMMARY OF THE INVENTION

The present invention provides a method, instrument, and kit for applying heat to the loop portion of a suture used to close a wound so as to melt the suture material, causing the loop to rupture. The cutting method disclosed and associated instrument allow the suture to be separated while producing less tension in the suture than current methods, thereby minimizing patient discomfort, tissue disruption and bleeding.

In a preferred method of the instant invention; a resistive heating element is brought into contact with the loop of a suture used to close a wound. The heating element is placed under the suture loop (or stitch), preferably between the patient's skin and a knotted portion of the suture. Power is supplied to the heating element for a brief time, during which the element heats and melts the suture in contact therewith, causing the loop to rupture. Thereafter, the suture is removed in the usual manner, i.e., using forceps or the like to extract the remaining suture material.

Accordingly, the present invention provides a suture removal instrument comprising:
(a) an elongated body having a proximal handle portion and insulated distal portion;
(b) a first conductive member extending from the insulated distal portion of the elongated body, terminating in a wedge-shaped tip;
(c) a resistive heating element extending alongside the first conductive member and affixed at its distal end to the wedge-shaped tip;
(d) conduction means for supplying power to the heating element;
(e) activation means for controlling the supply of power to the heating element; and
(f) circuitry for providing power to the heating element as pulses of high current of a predetermined duration.

The elongated body may serve as a handle for the operator to grasp and/or as a housing for the operating components, such as the power source, circuitry, conduction means and activation means. The elongated body may be formed from any suitable medical-grade material, such as plastic, metal, polycarbonate, polyvinyl chloride, and the like.

The conductive member is shaped to facilitate insertion thereof into (or under) a suture loop. In a preferred embodiment, the suture removal instrument comprises a pair of linear conductive members disposed in a parallel. The tapered, wedge-shaped tip of the first conductive member allows it to gently slide under the loop of the suture, between the patient's skin and a knotted portion of said suture. For example, the tapered tip may comprise a conical point. Alternatively, the tip may include one or more beveled surfaces which form a more or less wedge-shaped distal end.

The resistive heating element is preferably a thin filament, formed from a material such as nichrome, tungsten, nickel, stainless steel or the like. In a preferred embodiment, the resistive heating element extends in a linear fashion between first and second conductive members, being affixed at its proximal end to the distal end of the second conductive member and at its distal end to the tapered tip of the first conductive member. See, for example, FIG. 3. The resistive heating element preferably joins the tapered, wedge-shaped tip of the first conductive member to form an acute angle with the longitudinal axis of the first conductive member, on the surface adjacent to the tapered tip. The acute angle formed between the resistive heating element and the first conductive member preferably ranges from about 5 to about 40 degrees. The resistive heating element may have a constant or uniform cross-sectional area, or have one or more portions of reduced area, wherein heating preferentially occurs.

The power source required to heat the resistive heating element may be carried by the suture removal instrument itself. For example, in a preferred embodiment, the power source comprises one or more batteries, for example, rechargeable batteries, contained within the elongated body. Alternatively, the elongated body may be fitted with a standard power cord and connector adapted for use with a conventional wall outlet.

The circuitry ensures the heating of a heating element to a predetermined temperature suitable for thermally rupturing suture materials when the heating element resistance and source voltage fall within predetermined ranges. The circuit may be a timer circuit which connects power from the source to the heating element for a predetermined period of time. In a preferred embodiment, the circuit supplies a predetermined amount of electrical energy to the heating element such that the element reaches a predetermined temperature, the circuit having a means for modifying its output based on the resistance of the element so as to achieve the predetermined energy value. In a preferred embodiment, the circuitry also has a timing means which prevents a second activation until a predetermined time has elapsed following a first activation so as to thereby prevent heating of the conductive member distal tip to temperatures which could potentially burn a patient.

The conduction means for supplying power (typically electrical power) to the heating element may take any suitable form. Examples of suitable conduction means include, but are not limited to, wires, conductive structural components, electrodeposited metal coatings and the like.

The activation means for controlling the supply of power to the heating element may take any suitable form. Examples of a suitable activation means include, but are not limited to, an actuator button, an on/off switch, and a foot pedal.

As noted above, the suture removal instrument may optionally include a second conductive member placed between the insulated portion of the elongated body and the resistive heating element. The second conductive member preferably extends from the insulated distal portion of the elongated body and is disposed next to the first conductive member in a parallel fashion. In operation, the conductive members are connected to the circuitry output so as to supply power to the heating element when the circuitry is activated. The conductive members do not heat up because they have a much larger cross-sectional area than the resistive heating element.

In a particularly preferred embodiment, the suture removal instrument comprises an elongated body forming a handle, and a demountable distal tip assembly. The handle portion contains a power source, circuitry and an activation button. The distal end of the handle portion has a mounting means and conduction means for removably mounting the distal tip assembly to the handle portion. The distal tip assembly has an elongated insulated portion. First and second conductive members protrude distally from the insulated portion. It is conceivable that the resistive heating element could be integral with the conductive members, or that a single conductive member could be used, with the proximal end of the heating element being connected directly to conduction means contained within the insulated portion of the elongated body.

In a preferred embodiment, the first conductive member is longer than the second conductive member and has a tapered distal end. Both the conductive members are preferably formed from an easily machined metallic material, such as brass or stainless steel, and should have good thermal conduction properties. Both the members have a coplanar axis with each other and with the proximal handle portion. The distal end of the second element is connected to the tapered distal end of the first elongated member by a thin resistive heating element. The thin resistive heating element forms an acute angle of about 5 to 40 degrees with the adjacent surface of the first elongated member. The first and second conductive members are connected to the power source and the activation button by a suitable conduction means discussed above. Because the conductive members have much larger cross-sections than the thin resistive heating element, the conductive members are not heated by the current. Because the element is energized for only a short period of time, heating of the conductive members by the filament is minimal.

The present invention also contemplates a number of optional features.

For example, the suture removal instrument of the present invention may optionally include a removably mounted magnifier assembly, optionally including a hinged lens for magnifying the distal end of the instrument and operative field of use.

The suture removal instrument may also be provided with a distally projecting light assembly for illuminating the operative field, the light assembly preferably comprising one or more of light units mounted on the side of the distal portion of the handle assembly.

In addition, the suture removal instrument of the present invention may include one or more indicator lamps, for indicating battery status and activation status, for example. Examples of suitable lighting means include light emitting diodes (LEDs) and incandescent lamps.

The suture removal instrument of the present invention may further be outfitted with an alarm means, preferably mounted in the instrument handle, that emits an audible signal when current is delivered to the resistive heating element in the distal tip.

The present invention also contemplates the provision of a charging cradle assembly for recharging the power source that coordinates with the suture removal instrument of the present invention, particularly receiving the proximal end of the elongated handle portion thereof.

Finally, the present invention provides a suture removal kit comprising:

(i) an elongated body comprising a proximal handle portion and distal portion configured to receive an insulated distal tip assembly, the body housing a first, rechargeable power source; a conduction means for delivering power from the first power source to a heating element; an activation means for controlling the supply of power to the heating element; and circuitry for providing power to the heating element as pulses of high current having a predetermined duration;

(ii) one or more insulated distal tip assemblies having a generally wedge-shaped distal end, comprising (i) a first conductive member terminating in a tapered distal tip and (ii) a resistive heating element extending alongside the first conductive member and affixed at its distal end to the distal end of the tapered distal tip, the tip assembly detachably mountable to the distal end of the elongated body; and (iii) a charging cradle connectable to a second, external power source for recharging the first power source housed within the elongated body.

In a preferred embodiment, the suture removal kit of the present invention is provided with multiple, single use distal tip assemblies In another preferred embodiment, the first power source comprises at least one rechargeable battery, optionally a removable battery pack. The charging cradle may be configured to receive either the elongated handle itself or the battery pack separately. The cradle may further be provided with one or more indicator lights, for indicating the status of the cradle and/or the first power source.

These and other objects and features of the invention will become more fully apparent when the following detailed description is read in conjunction with the accompanying figures and examples.

DETAILED DESCRIPTION OF THE PREFERRED EMBODIMENT

In the context of the present invention, the following definitions apply:

The term "suture" is used to refer both to the fine thread or other material used surgically to close a wound or join tissues and to the stitch so formed.

The term "distal" refers to that end or portion which is situated farthest from the hand of the operator and closest to the body of the patient when the device is in use.

The term "proximal" refers to that end or portion situated closest to the hand of the operator and farthest away from the body of the patient when the device is in use.

The accompanying figures, described in detail below, illustrate aspects of the invention but are in no way intended to limit the scope of the present invention.

Figure 1:
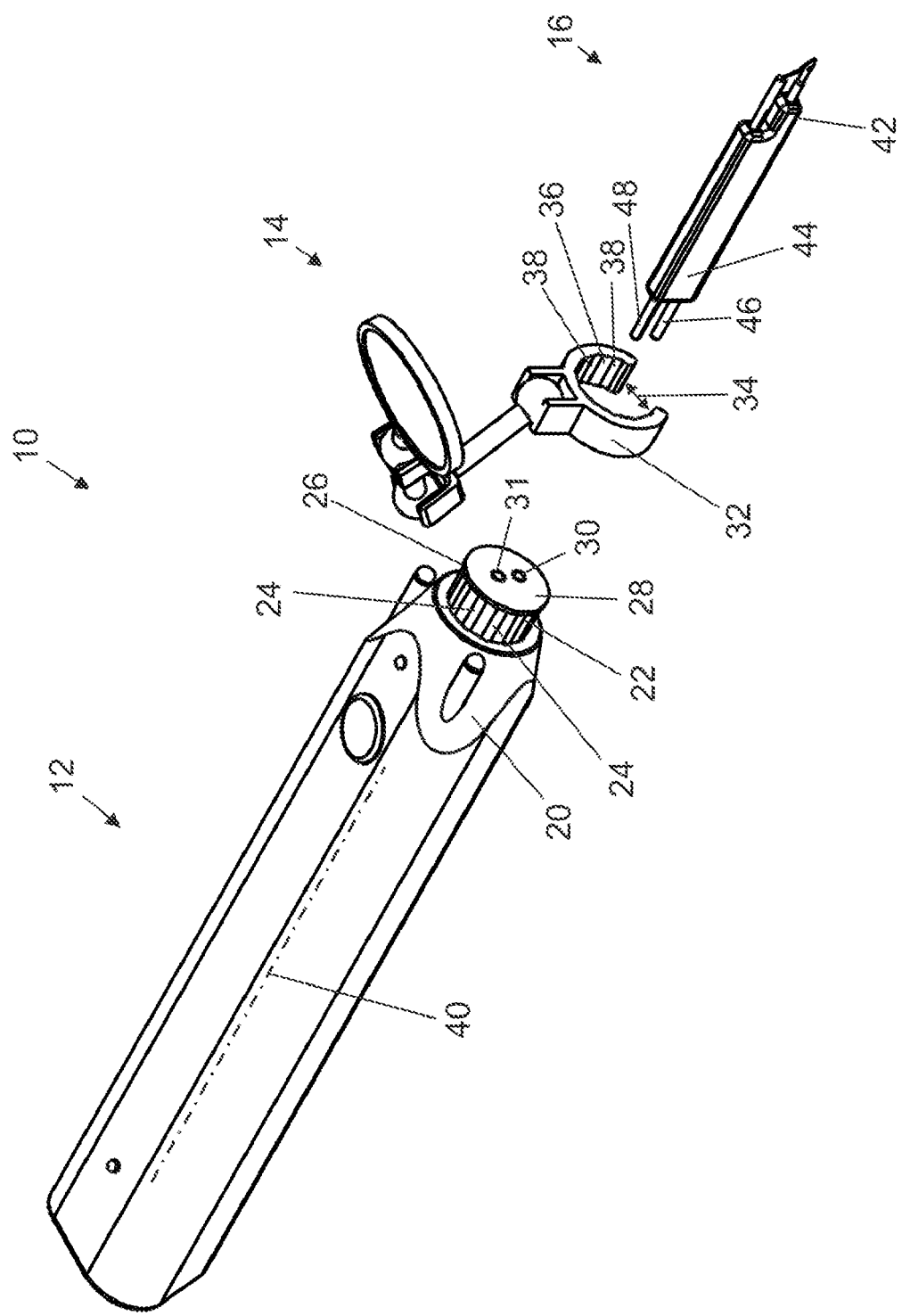
FIG. 1 is an exploded view of a suture cutter constructed in accordance with the principles of this invention.
Figure 2:
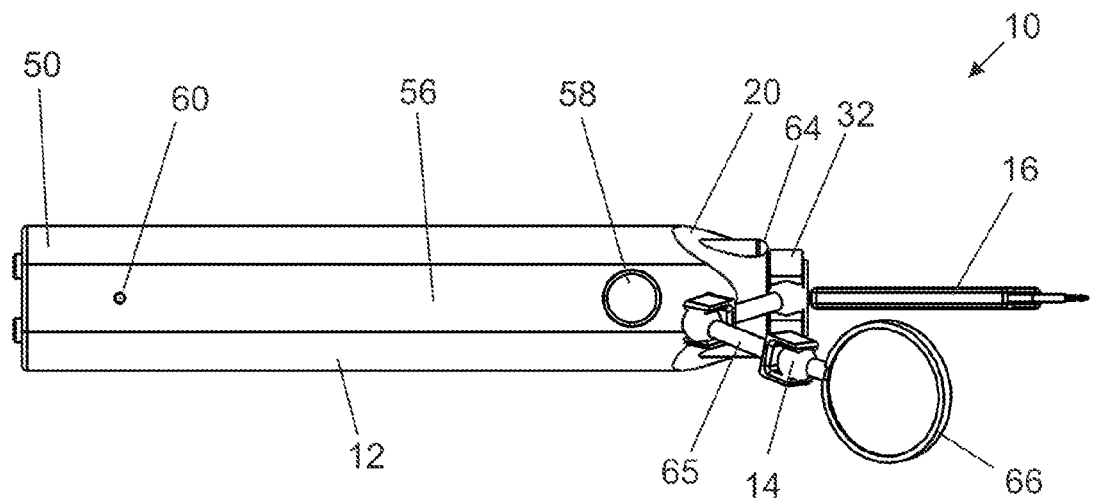
FIG. 2 is a plan view of the assembled objects of FIG. 1.
Figure 3:
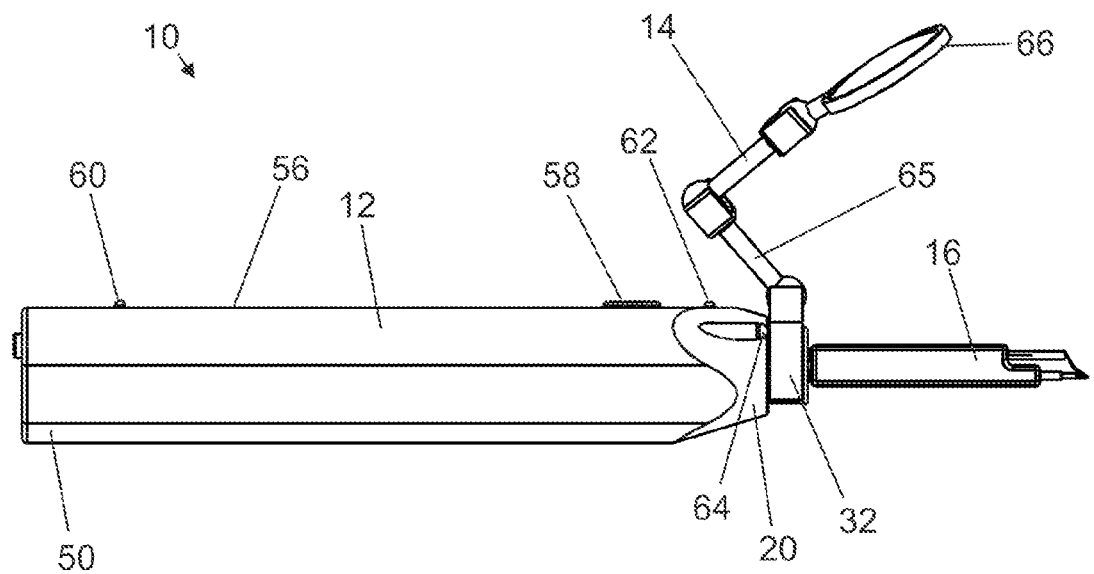
FIG. 3 is a side elevational view of the objects of FIG. 2.
Figure 4:
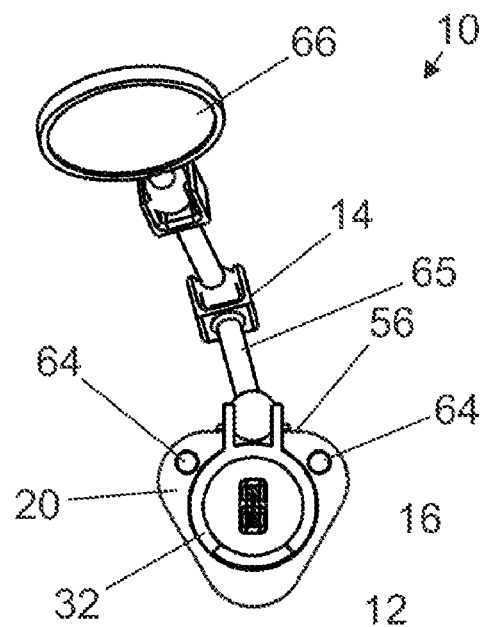
FIG. 4 is a distal axial view of the objects of FIG. 2.
Figure 5:
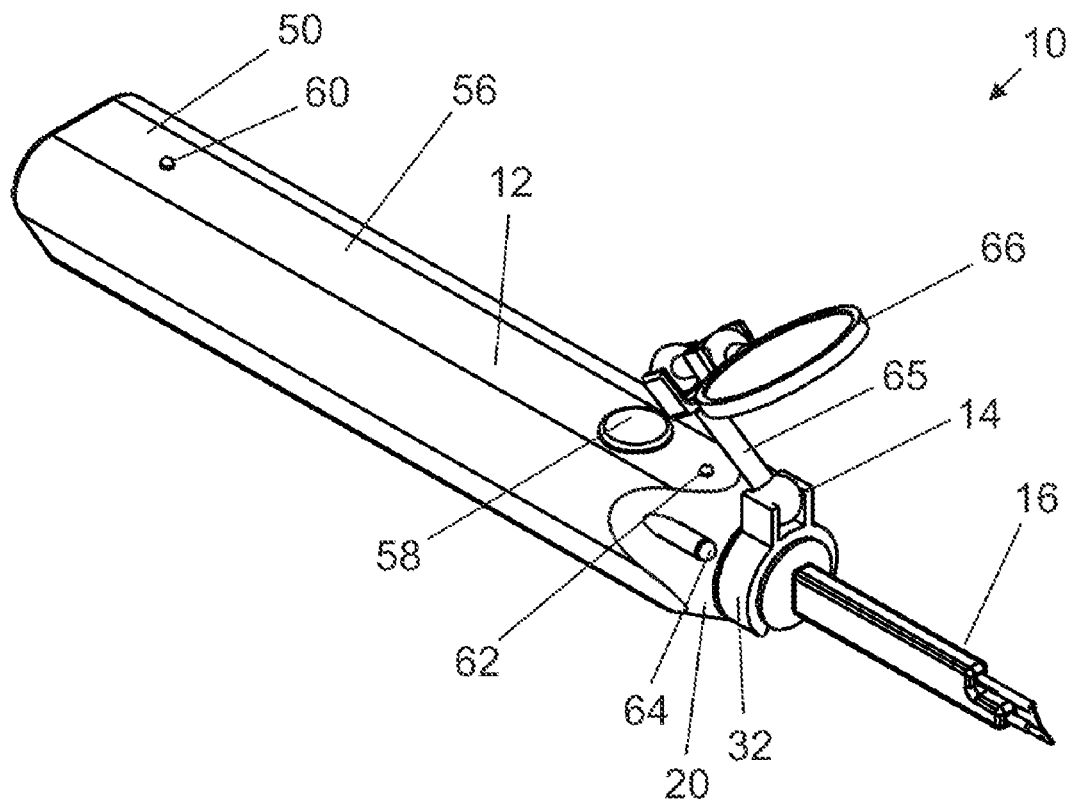
FIG. 5 is a perspective view of the objects of FIG. 2.
Figure 6:
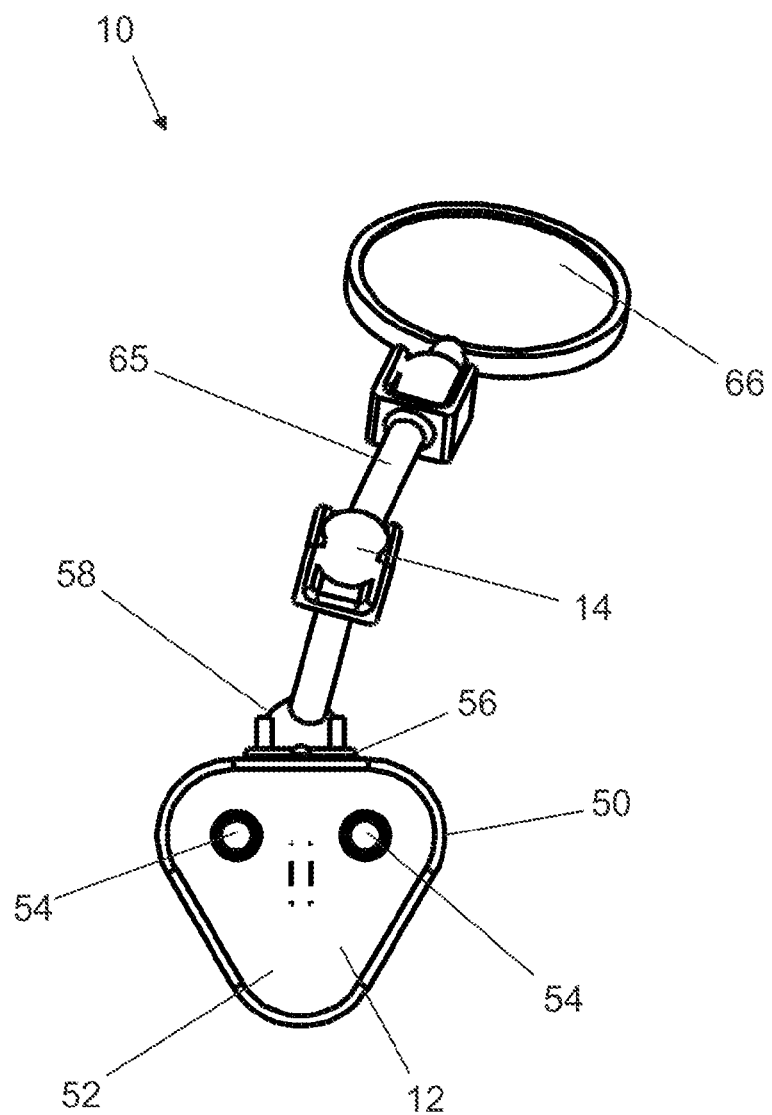
FIG. 6 is a proximal axial view of the objects of FIG. 2.
Figure 7:
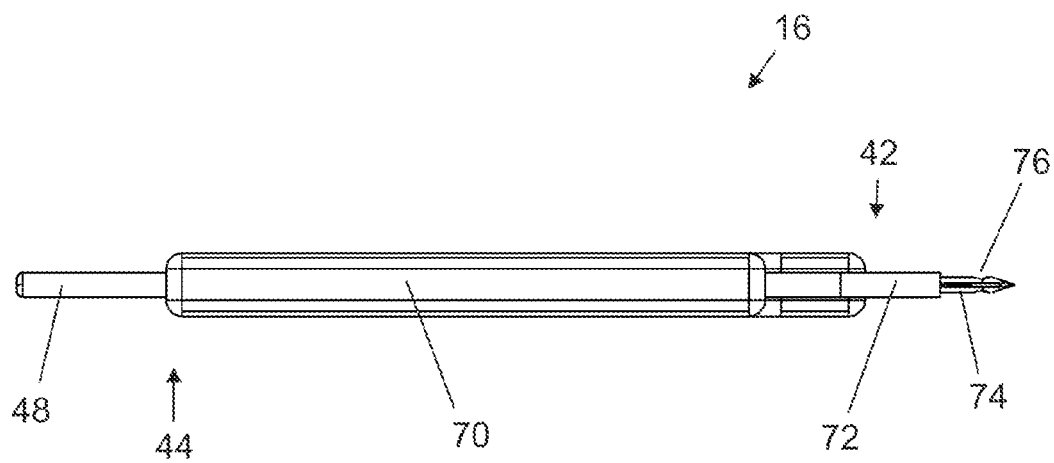
FIG. 7 is a plan view of the distal tip assembly of FIG. 1.
Figure 8:
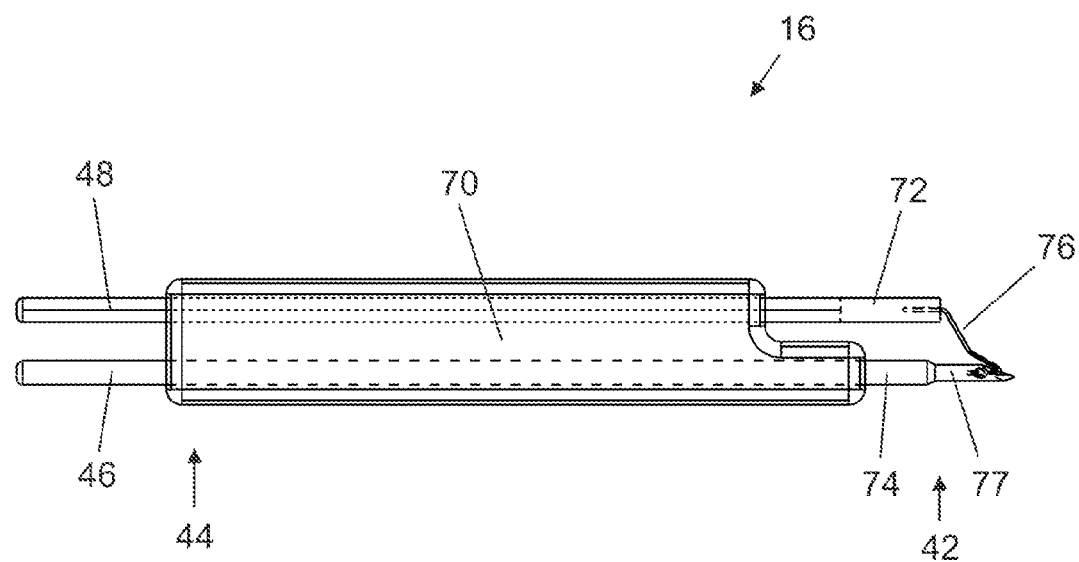
FIG. 8 is a side elevational view of the objects of FIG. 7.
Figure 9:
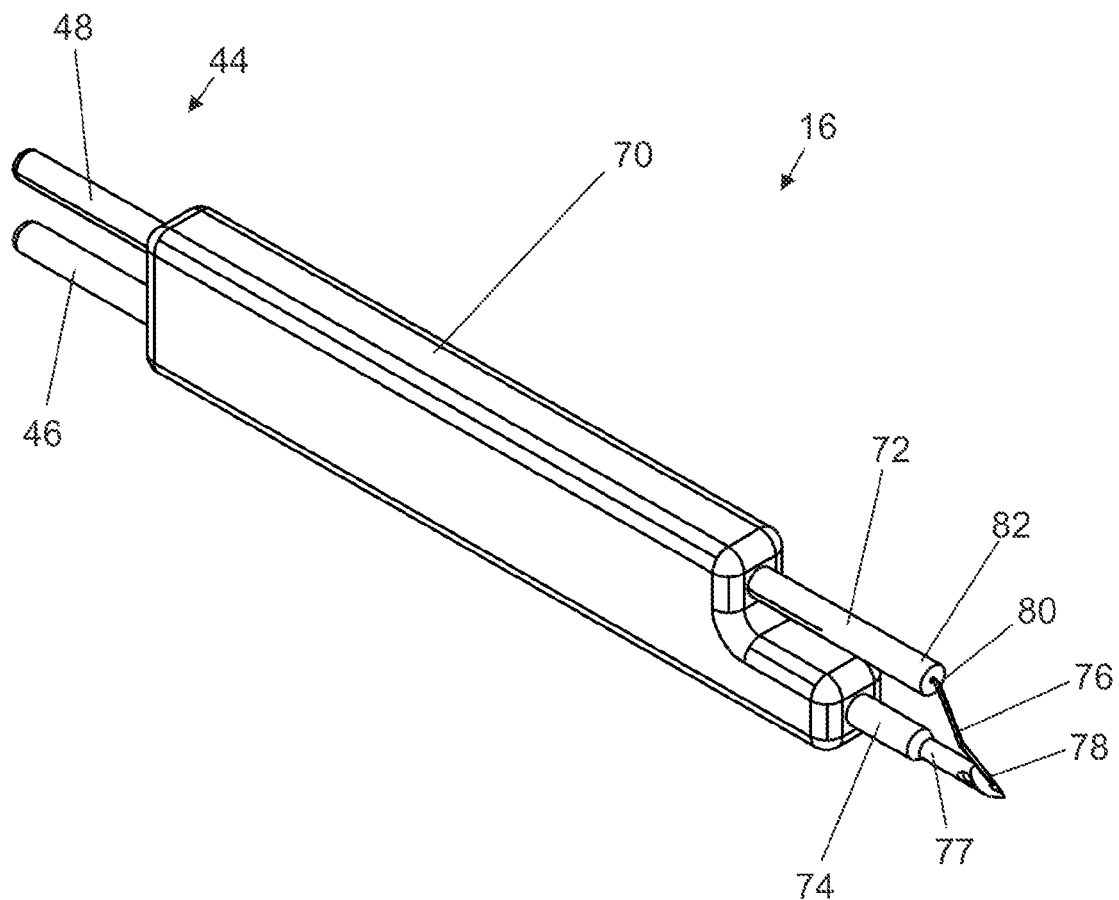
FIG. 9 is a perspective view of the objects of FIG. 7.
Figure 10:
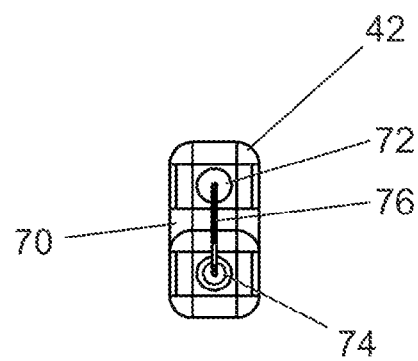
FIG. 10 is a distal end view of the objects of FIG. 7.
Figure 11:
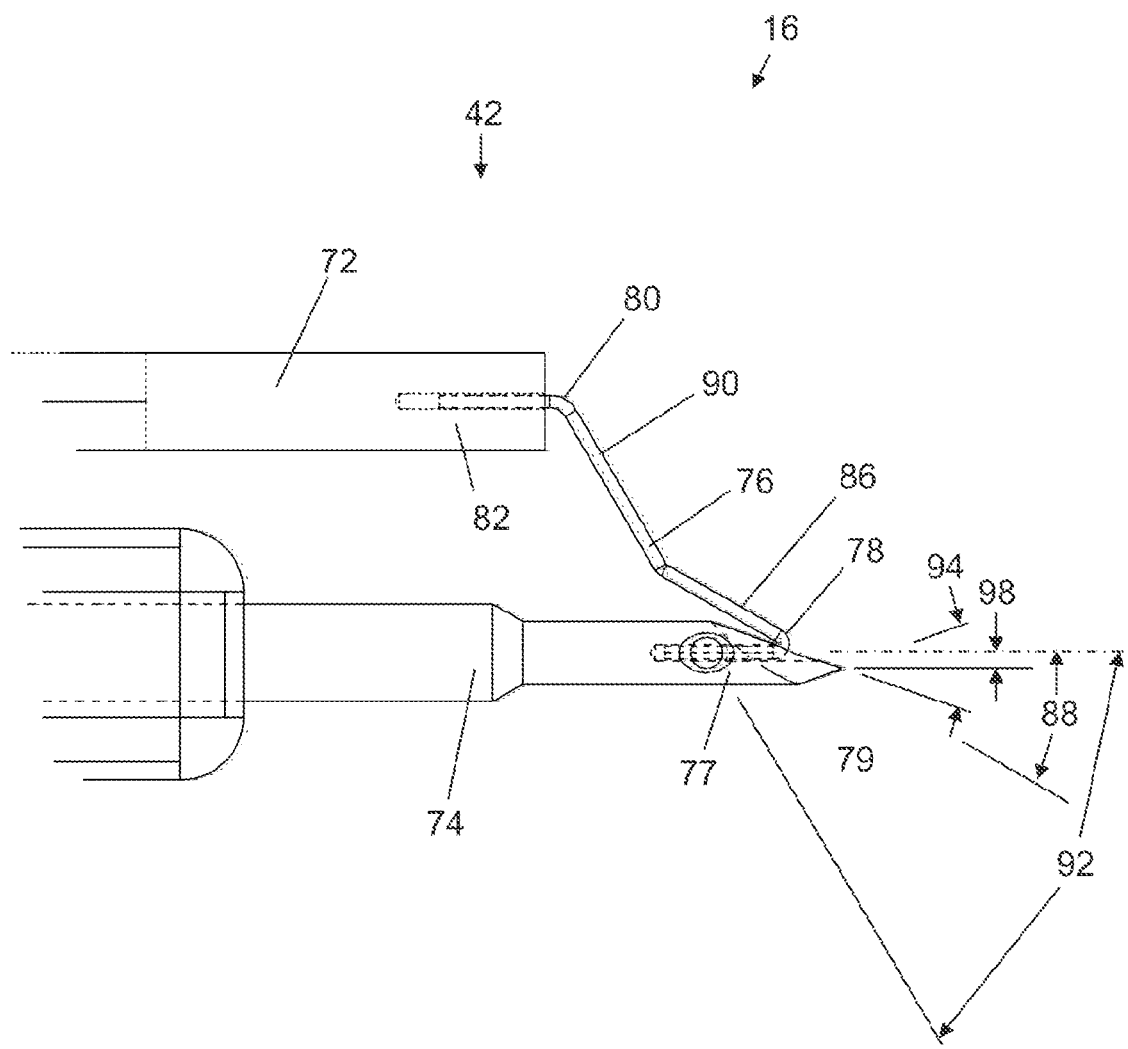
FIG. 11 is an expanded side elevational view of the distal portion of the objects of FIG. 7.
Figure 12:
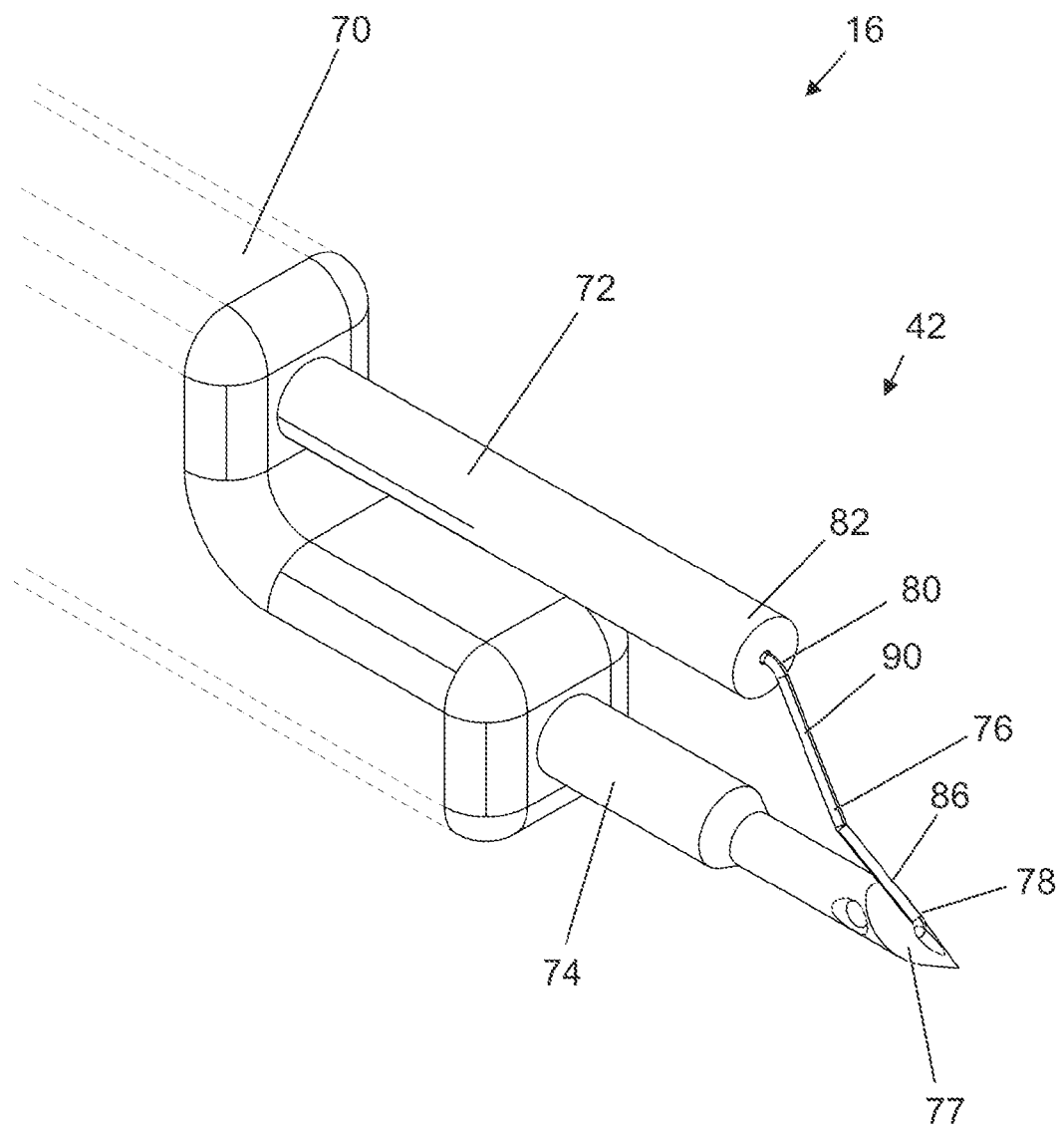
FIG. 12 is an expanded perspective view of the objects of FIG. 11.

Referring to the figures showing a suture cutter 10 constructed in accordance with the principles of this invention, FIG. 1 depicts an exploded view of suture cutter 10, cutter 10 having a first, proximal assembly 12 forming a handle, a second magnifier assembly 14, and a third, distal tip assembly 16. Handle portion 12 has a distal end 20 having a cylindrical portion 22 having a plurality of axial ribs 24 and a distal ridge 26 having a diameter slightly larger than cylindrical portion 22. Distal end 20 has a distal-most surface 28 in which are first connector socket 30 and second connector socket 31. Magnifier assembly 14 has a mounting ring 32 having a gap 34 and a cylindrical inner surface 36 having a diameter approximately equal to that of cylindrical portion 22 of distal end 20 of handle 12, and a plurality of axial grooves 38 corresponding and complementary in size and shape to ribs 24 of cylindrical portion 22 of distal end 20 of handle 12. Ring 32 is made from a suitable polymeric material. Ring 32 is mounted to distal end 20 of handle assembly 12, gap 34 allowing ring 32 to elastically deform to pass over distal ridge 26 so that ring 32 removably mounts to cylindrical portion 22 of distal end 20. Ring 32 is angularly positionable about axis 40 of cylindrical portion 22. Distal tip assembly 16 has a distal end 42 and a proximal end 44, proximal end 44 having a first axial connector piece 46 and a second axial connector piece 48. Distal tip assembly 16 is removably mounted to distal end 20 of handle assembly 12, with first connector piece 46 mounting to first connector socket 30, and second connector piece 48 mounting to second connector socket 31.

Friction between connector piece 46 and socket 30 and between connector piece 48 and connector socket 31 maintains the positional relationship between handle assembly 12 and distal tip assembly 16, as well as provides electrical connectivity therebetween. In other embodiments, a fastening means may be provided to maintain the positional relationship. For instance, distal tip assembly 16 may be removably mechanically fastened to handle assembly 12 using screws, clips, or the like; alternatively, assemblies 12 and 16 may be provided with mating interlocking features such as slots and ribs, threaded portions, or the like. Electrical connectivity between assemblies 12 and 16 may take the form of mating pairs of contacting concentric cylindrical surfaces, planar surfaces, protrusions, or the like in other embodiments.

The means for mounting magnifier assembly 14 to handle assembly 12 may be modified in other embodiments. For instance, ribs 24 of cylindrical portion 22 of distal end 20 of handle 12, and grooves 38 of inner surface 36 of ring 32 may be eliminated, and the diameter of inner surface 36 made somewhat smaller than the diameter of cylindrical portion 22 so that the frictional force between surface 36 and portion 22 is sufficient to maintain angular positioning therebetween. In other embodiments, the magnifier assembly 14 may be removably mounted to handle 12 by other mechanical means, such as mating protrusions and sockets, or mechanical fasteners, such as screws or clips.

Referring now to FIGS. 2 through 6 showing suture cutter 10, magnifier assembly 14 and distal tip assembly 16 are removably mounted to distal end 20 of handle assembly 12. Handle 12 has a proximal end 50 having a proximal-most surface 52 in which are electrical connectors 54. Upper surface 56 of handle 12 has protruding therefrom activation button 58, first indicator lamp 60, and second indicator lamp 62. Near distal end 20, illumination lamps 64 face toward the distal end 42 of cutter 12. In a preferred embodiment, lamps 64 are light emitting diodes (LEDs). In another, they are incandescent lamps. Ring 32 of magnifier assembly 14 has mounted thereto positioning linkage 65 having at its distal end magnifying lens 66. Linkage 65 allows lens 66 to be positioned and pivoted so as to allow distal end 42 of distal tip assembly 16 to be viewed in magnification through lens 66.

Figure 13:
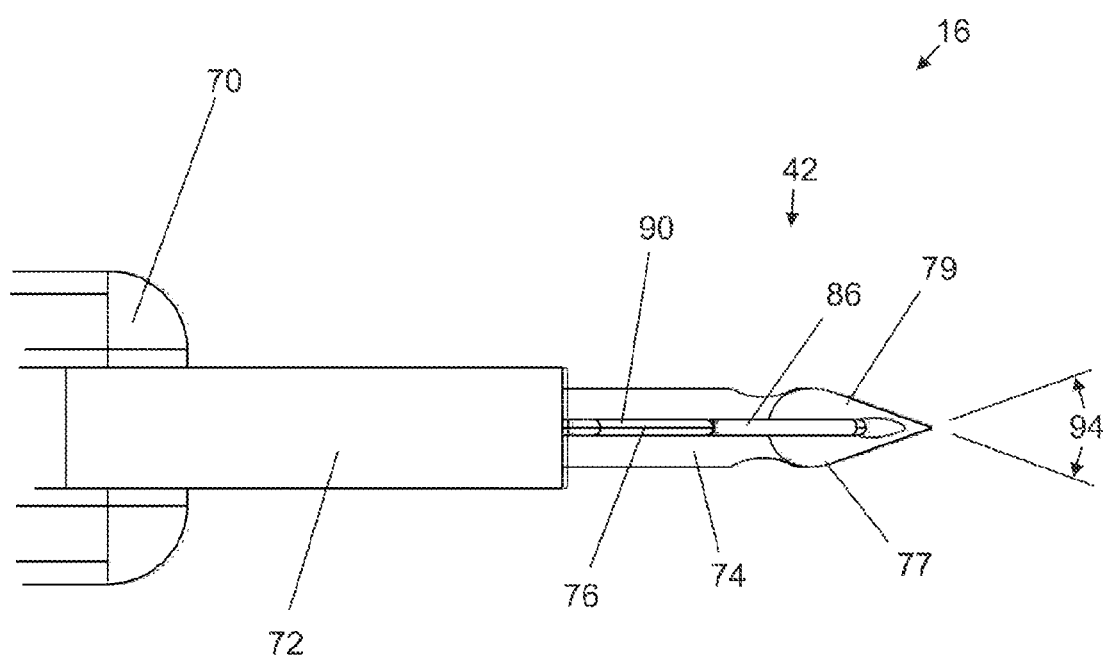
FIG. 13 is a plan view of the objects of FIG. 11.

Referring now to FIGS. 7 through 12, distal tip assembly 16 has a body 70 made of a suitable dielectric material. In a preferred embodiment body 70 is made of a polymeric material. First connector piece 46 forms the proximal end of first conductive piece 74; second connector piece 48 forms the proximal end of second conductive piece 72. In a preferred embodiment body 70 is molded around conductive pieces 72 and 74. Distal end 42 of assembly 16 is generally wedge-shaped when viewed in a side elevational view as in FIG. 8, the wedge being formed by the distal portion of first conductive piece 74 and heating element 76. Heating element 76, formed from a material such as nichrome, tungsten, nickel, stainless steel or the like, has a distal end 78 affixed to distal end 77 of first conductive piece 74. Proximal end 80 of element 76 is affixed to distal end 82 of second conductive piece 72. Distal end 82 of second conductive piece 72 is displaced proximally distance 84 from distal end 77 of first connector piece 74. In a preferred embodiment, distal portion 86 of element 76 forms a first wedge angle 88 with first conductive piece 74. Proximal portion 90 of element 76 forms a second wedge angle 92 with first conductive piece 74. In a preferred embodiment proximal end 80 of element 76 is affixed to distal end 82 of second conductive piece 72, such as by crimping, piece 72 being made of a malleable, low resistivity material, such as brass. Also in a preferred embodiment distal end 78 of element 76 is affixed to distal end 77 of first conductive piece 74, such as by crimping, piece 74 also being made of a low resistivity material, such as brass. In other embodiments, conductive pieces 72 and 74 are made from stainless steel, nickel, or other suitable corrosion resistant alloys, or of assemblies having an electrically conductive portion of a first material, and second portion made of a suitable material such as, for instance, a ceramic or polymeric material, or a corrosion resistant metal. In other embodiments, element 76 may be affixed to conductive pieces 74 and 72 by welding, brazing or soldering. Distal end 77 of first conductive piece 74 has a tapered distal-most portion 79 having a more or less conical shape having an included angle 94 and an axis 96 offset distance 98 from axis 100 of distal end 77 of conductive piece 74. Included angle 94 is less than twice first wedge angle 88 so that element distal portion 86 contacts tapered distal-most portion 79 of conductive piece 74 only at the point of attachment. When viewed in a plan view as shown in FIG. 13, tapered portion 79 of distal end 77 of first conductive piece 74 forms a wedge having an included angle 94 equal to included angle 94 of the conical shape of tapered portion 79 of conductive piece 74.

Handle portion 12 optionally contains at least one battery which is charged by a suitable charging means, for example, a charging cradle, connected to the at least one battery by connectors 54 in proximal-most surface 52. In other embodiments charging may be accomplished through electromagnetic coupling with an external charger and connectors 54 may be eliminated. First indicator light 60 indicates the battery condition. The at least one battery is connected to circuitry having a means for providing high current output when activated. The circuitry output is connected via a connecting means to electrical connectors 30 and 31 in distal-most surface 28 of handle 12, and, via connector pieces 46 and 48 of tip assembly 16 to conductive pieces 74 and 72 respectively. In this manner, the output of the circuitry is supplied to heating element 76 when the circuitry is activated, activation occurring when button 58 is depressed. The circuitry of handle 12 also has a current control means therein, such that activation of the circuitry causes voltage to be supplied to heating element 76 for a period of time determined by the current control means. In a preferred embodiment the time is about 0.1 to 1 seconds, or more preferably between 0.1 and 0.5 seconds. During the time that voltage is supplied to heating element 76, second indicator lamp 62 is illuminated and an audio signal is emitted by a means within handle 12. The circuit of handle 12 further contains a timing means such that a second activation of the device is prevented for a predetermined period of time after a first activation. In a preferred embodiment the period between activations is about 1 to 5 seconds, and more preferably between 1 and 3 seconds.

Figure 14:
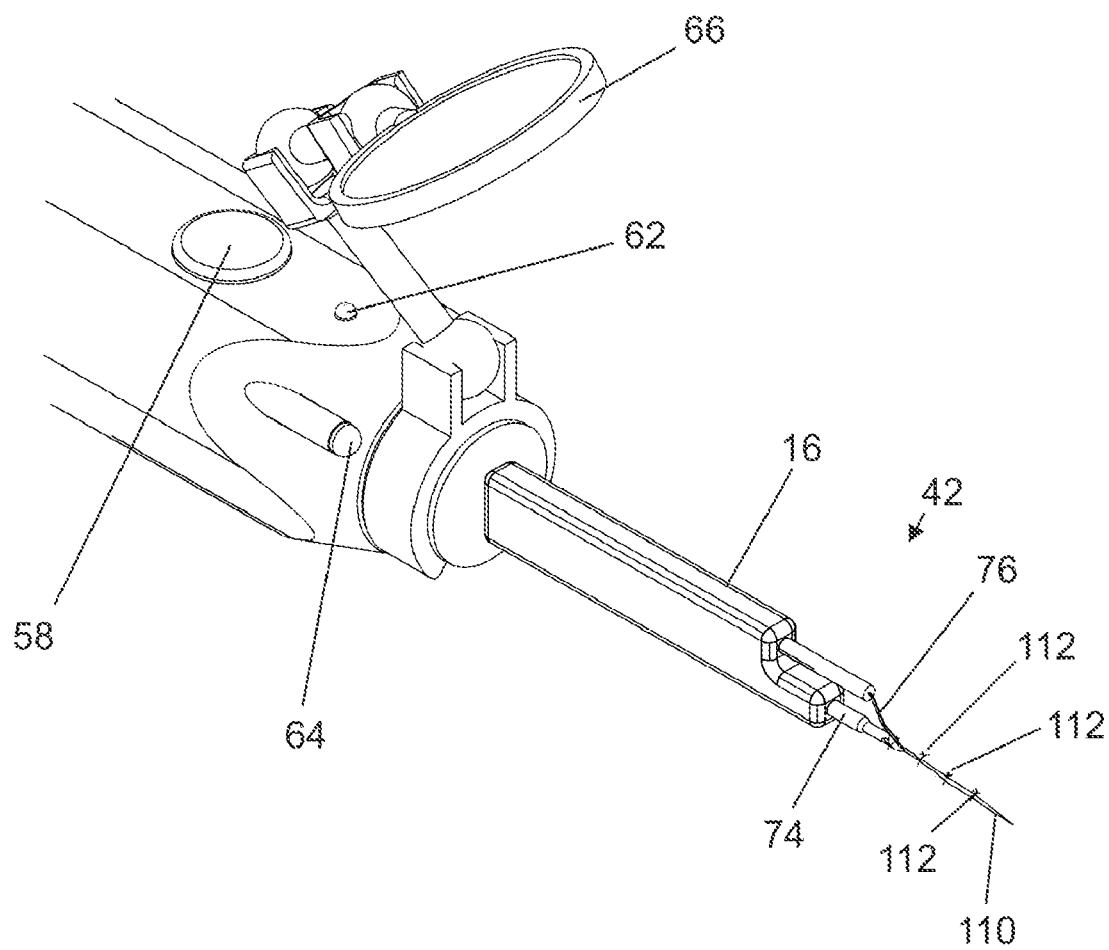
FIG. 14 is an expanded perspective view of a suture cutter constructed in accordance with the principles of this invention in use cutting a suture.
Figure 15:
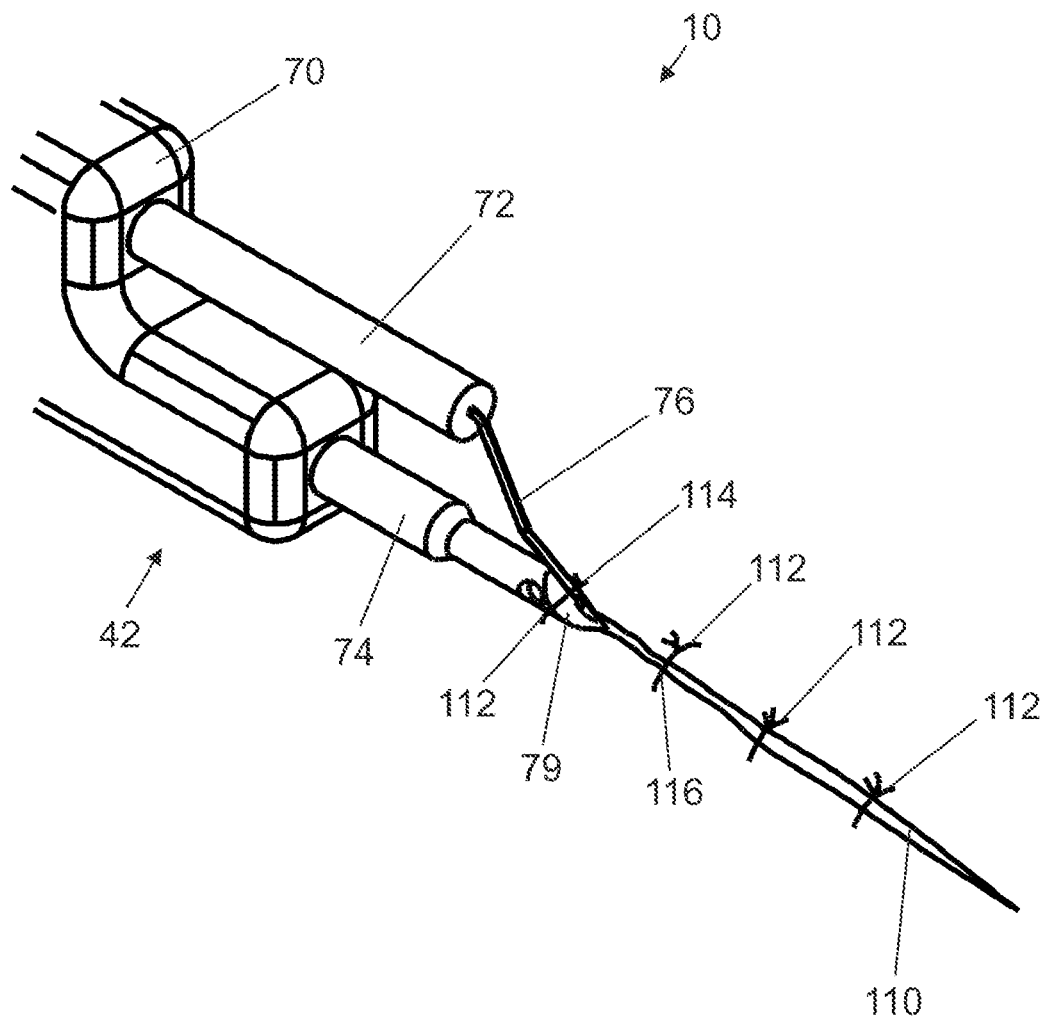
FIG. 15 is an expanded perspective view of the objects of FIG. 14.

Referring now to FIGS. 14 and 15 showing suture cutter 10 in use, magnifier 66 is aligned so as to allow magnified viewing of distal end 42 of tip assembly 16, lights 64 providing supplemental illumination to the region. Wound 110 is closed by sutures 112. Tapered distal-most portion 79 of first conductive piece 74 is inserted into the loop of stitch 114 and advanced until suture 114 is in contact with heating element 76, whereupon activation button 58 is depressed. Depressing button 58 causes voltage to be supplied to heating element 76 causing element 76 to heat thereby melting the portion of suture 114 in contact with element 76 causing it to rupture. First activation light 62 is lit, and a means within handle 12 emits an audible signal during heating of element 76. Cutter 10 is then repositioned so that tapered distal-most portion 79 of first conductive piece 74 is inserted under stitch 116 in the same manner as for stitch 114. Stitch 116 is then cut in the same manner as stitch 114. When all the stitches are cut, they are removed in the conventional manner, using a forceps or other grasping device.

The temperature of heating element 76 is non-uniform throughout its length. Conductive pieces 72 and 74 have large thermal masses and high thermal conductivity as compared to element 76. Because of this, heat flows from element 76 into conductive pieces 72 and 74, thereby causing cooling of filament 76 in portions of element 76 adjacent to conductive pieces 72 and 74. Heat flow from element 76 into conductive pieces 72 and 74 also heats up the portions of these pieces adjacent to filament 76, particularly distal portion 77 of first conductive piece 74 which has less thermal mass than the distal portion of second conductive piece 72. Tapered distal-most portion 79 of first conductive piece 74 undergoes the most heating. The temperature at a given location on filament 76 is determined by its distance from conductive pieces 72 and 74, the voltage applied to element 76, and the length of time that the voltage is applied. At the first instant that voltage is applied to filament 76, the temperature in the filament is quite uniform and the distal portions of conductive pieces 72 and 74 have only a slight temperature increase, as little heat transfer from filament 76 to conductive pieces 72 and 74 has occurred. Increasing the voltage applied to a given heating element will increase the temperatures; however, at the first instant of activation, the temperature distribution along the filament length is uniform. When voltage is applied for longer periods of time to a heating element, such as element 76, the temperature of the element increases until it reaches equilibrium, wherein the rate of radiant and convective heat losses from the element then being equal to the electrical power input. The temperature distribution in the element 76, however, becomes increasingly non-uniform. Portions adjacent to conductive pieces 72 and 74 are cooler because of conductive heat loss to the conductive pieces. Distal portions of conductive pieces 72 and 74 are heated by this conductive transfer of heat. Suture cutter 10 cuts sutures using the portion of distal portion 86 in close proximity to distal portion 77 of first conductive piece 74.

It is essential that suture cutter 10 rapidly and efficiently melt a suture so as to cut it, yet at the same time not burn the patient. Accordingly, it is essential that heat transfer from heating element 76 to conductive distal portion 77 of first conductive piece 74 be minimized. This is accomplished by applying a high current, supplied by circuitry inside handle 12 to filament 76, for a short period of time so as to maximize filament temperature while minimizing conductive heat loss. When the power to element 76 ceases, the element quickly cools through conduction of heat from element 76 to distal portions of conductive pieces 72 and 74. Because a voltage pulse is supplied to the filament for a brief period of time to melt suture, the amount of heat energy in the filament is minimized. The thermal mass of the distal ends of conductive pieces 72 and 74 is much greater than that of filament 76. Because of these factors, the temperature rise of the distal end of conductive piece 74, especially of tapered region 79 is insufficient to cause patient discomfort due to contact with region 79. The minimum time between activations produced by the timing means within handle 12 ensures that heat conduction from distal portion 77 of conductive piece 74 decreases the temperature of distal portion 77 so that subsequent activation does not cause sufficient temperature rise in portion 77 to cause patient discomfort.

Figure 16:
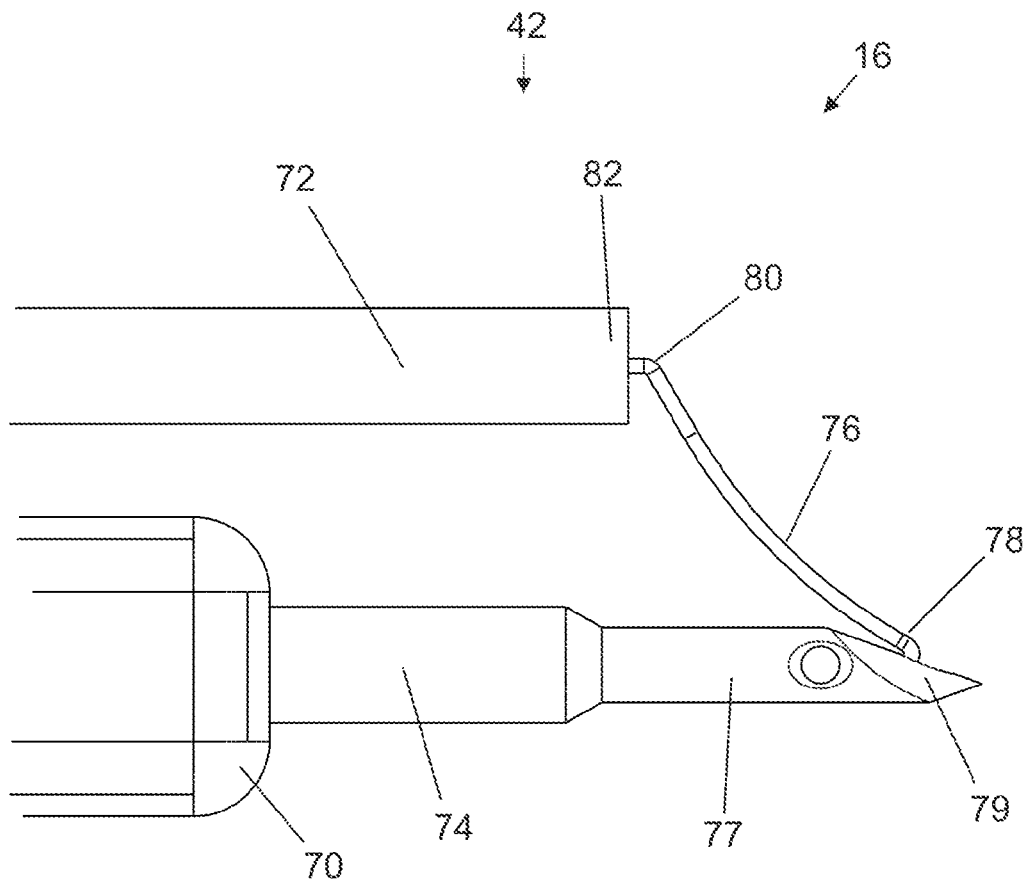
FIG. 16 is an expanded side elevational view of the distal portion of the distal tip assembly of an alternate embodiment.
Figure 17:
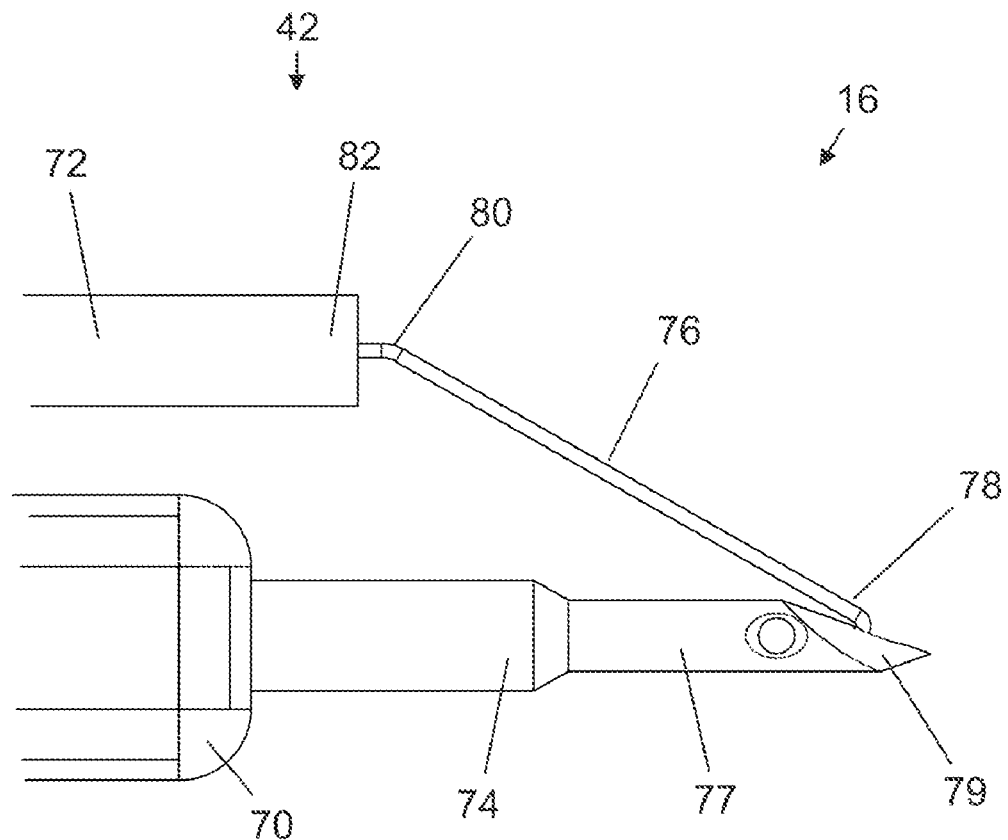
FIG. 17 is an expanded side elevational view of the distal portion of the distal tip assembly of another alternate embodiment.

The wedge shape of distal portion 42 of tip assembly 16 when viewed in side elevation (FIG. 11) and when viewed in plan view (FIG. 13) allows cutter 10 to penetrate the loop of a suture with distal-most portion 79 of first conductive piece 74, and advance within the loop until filament 76 contacts the suture and cutting is accomplished. In the embodiment previously herein described, element 76 has linear proximal and distal portions. Embodiments having elements 76 with other shapes are contemplated. For instance, FIG. 16 shows a tip assembly 16 having an element 76 with a curvilinear shape. FIG. 17 shows a tip assembly 16 with an element 76 having a single linear portion. In both of these embodiments the element 76 and first conductive piece 74 form a wedge when viewed in side elevation. Other element shapes may be used provided they have a distal portion 78 which forms a taper or wedge shape with conductive piece 74 when viewed in side elevation.

Distal-most portion 79 of first conductive piece 74 also has a wedge shape when viewed in side elevation (FIG. 11) and when viewed in plan view (FIG. 13) which allows cutter 10 to penetrate the loop of a suture with distal-most portion 79 of first conductive piece 74, and advance within the loop until filament 76 contacts the suture and cutting is accomplished.

Figure 18:
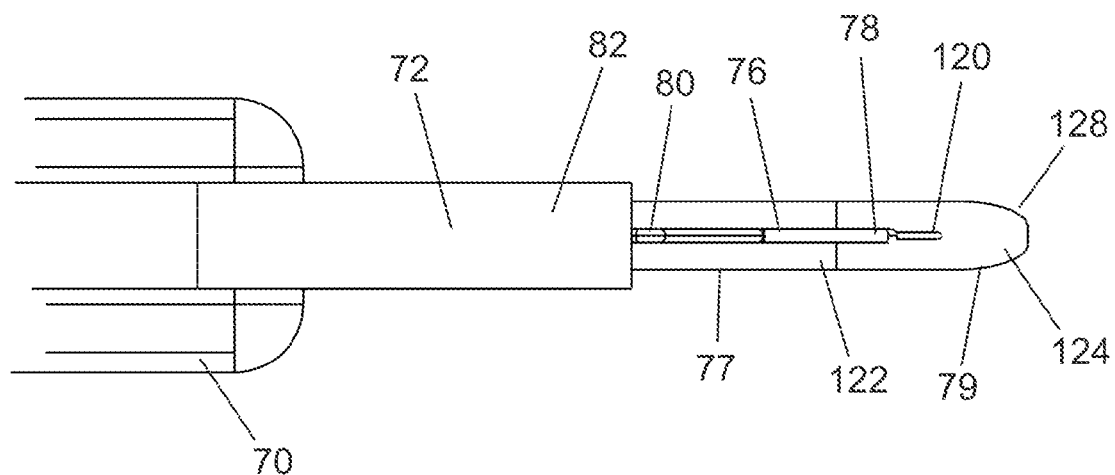
FIG. 18 is an expanded plan view of the distal portion of the distal tip assembly of an alternate embodiment.
Figure 19:
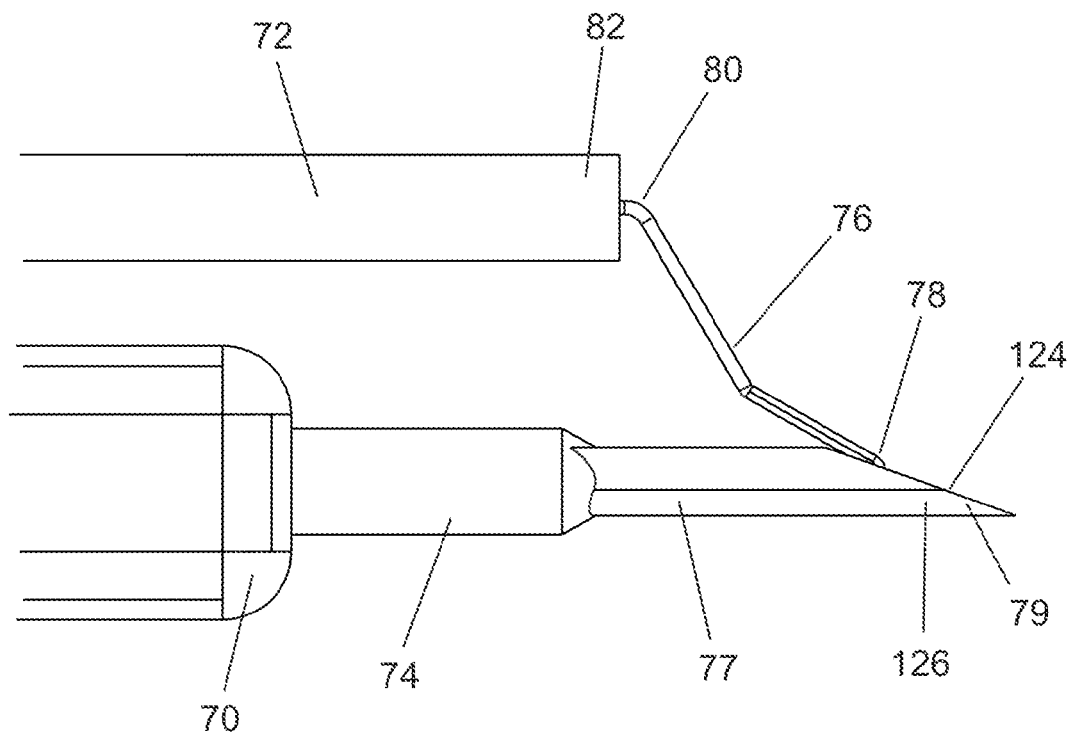
FIG. 19 is a side elevational view of the objects of FIG. 18.
Figure 20:
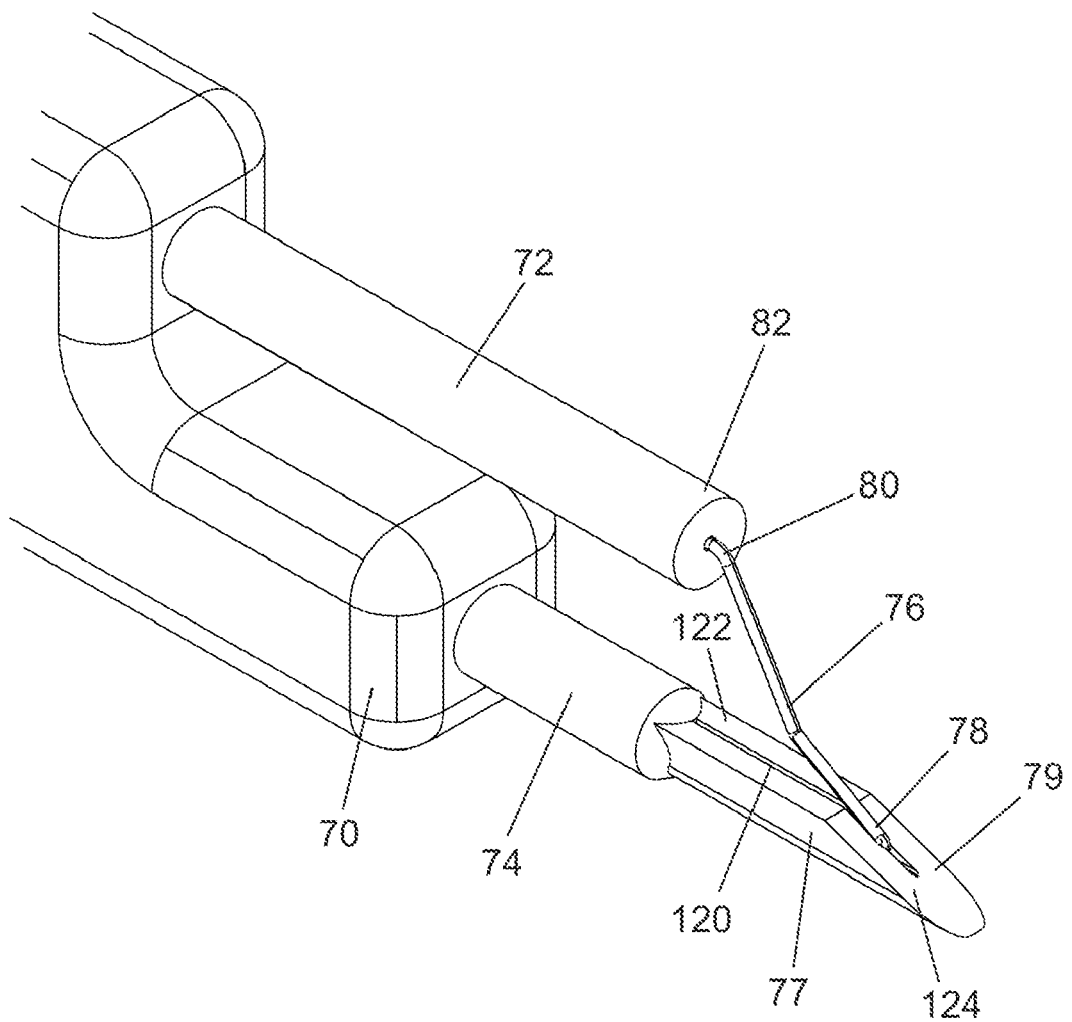
FIG. 20 is a perspective view of the objects of FIG. 18.
Figure 21:
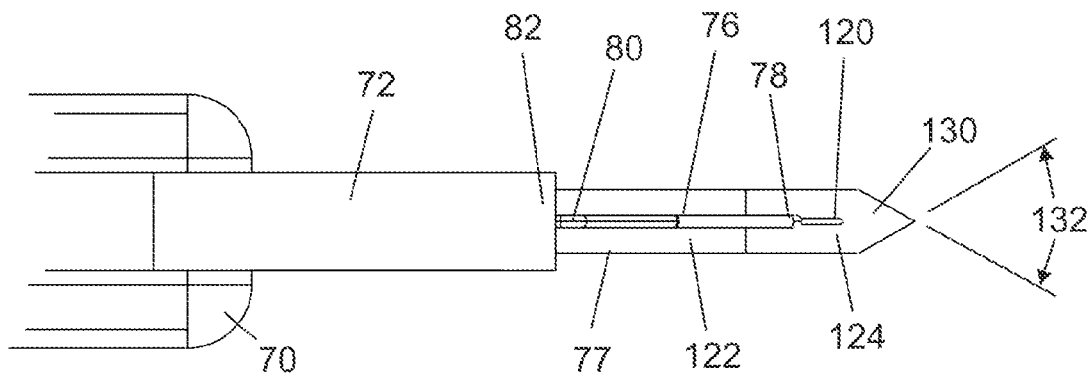
FIG. 21 is an expanded plan view of the distal portion of the distal tip assembly of another alternate embodiment.
Figure 22:
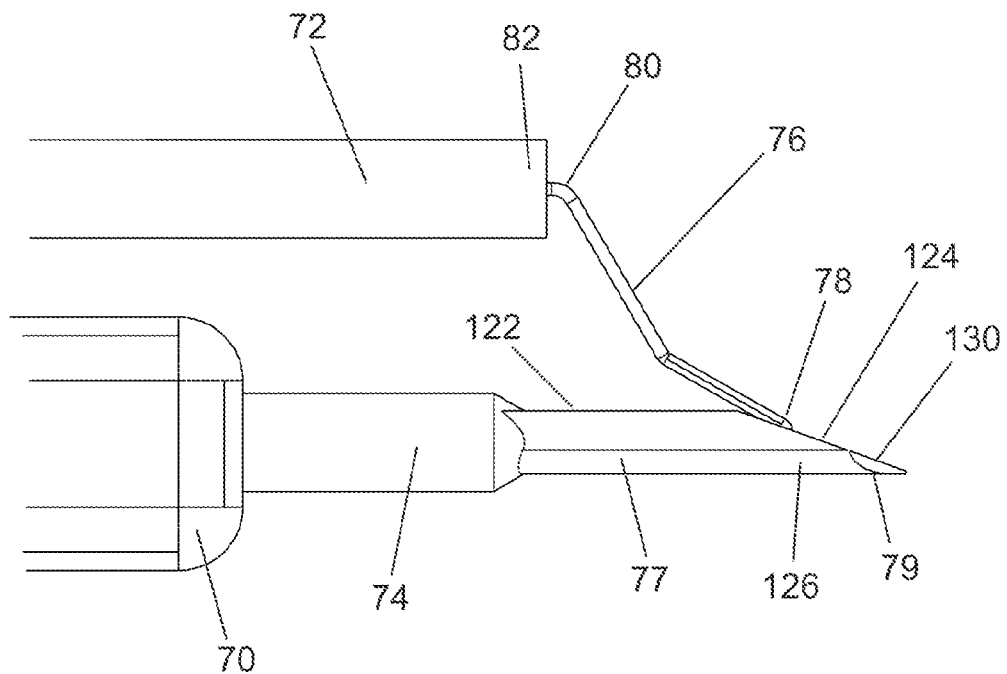
FIG. 22 is a side elevational view of the objects of FIG. 21.
Figure 23:
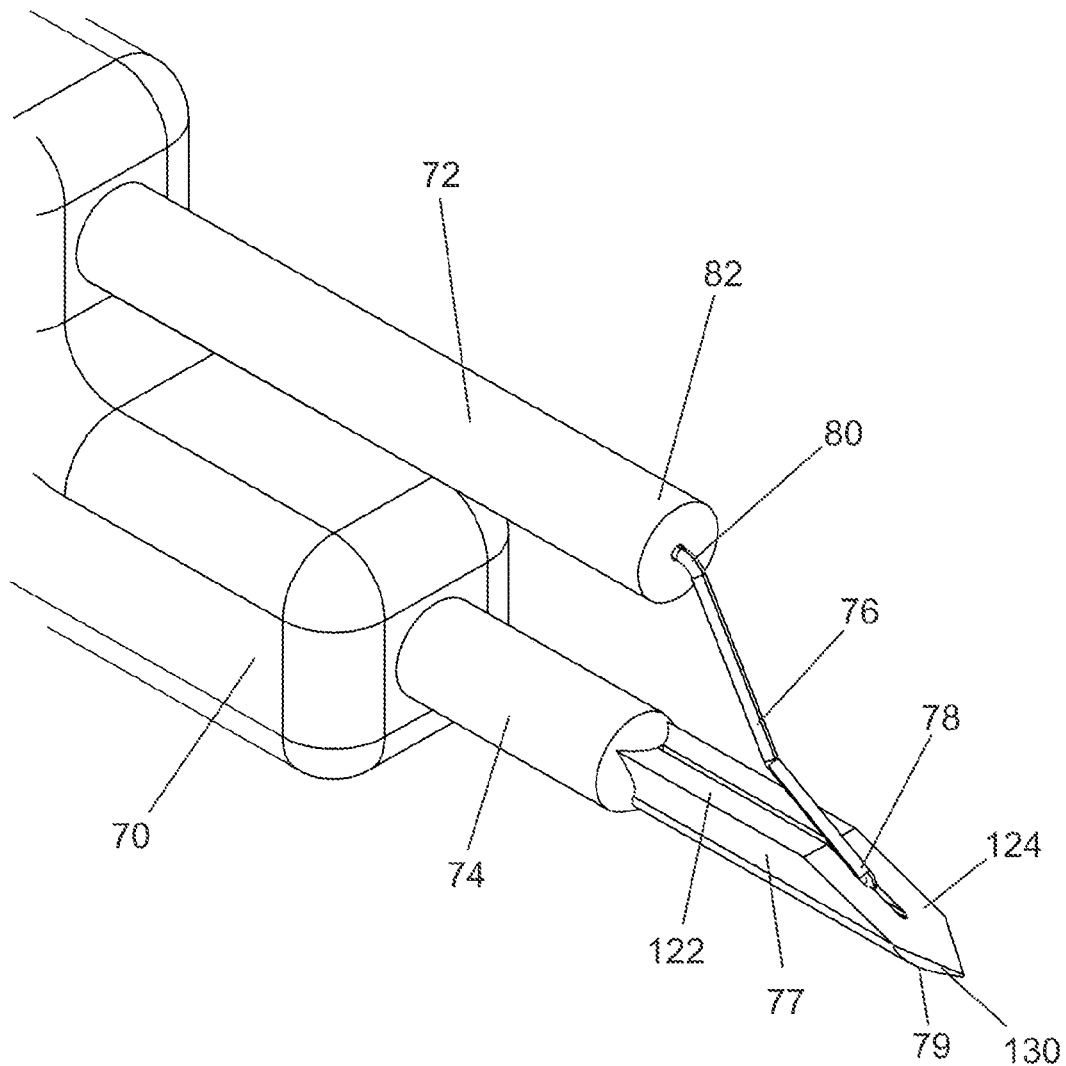
FIG. 23 is a perspective view of the objects of FIG. 21.
Figure 24:
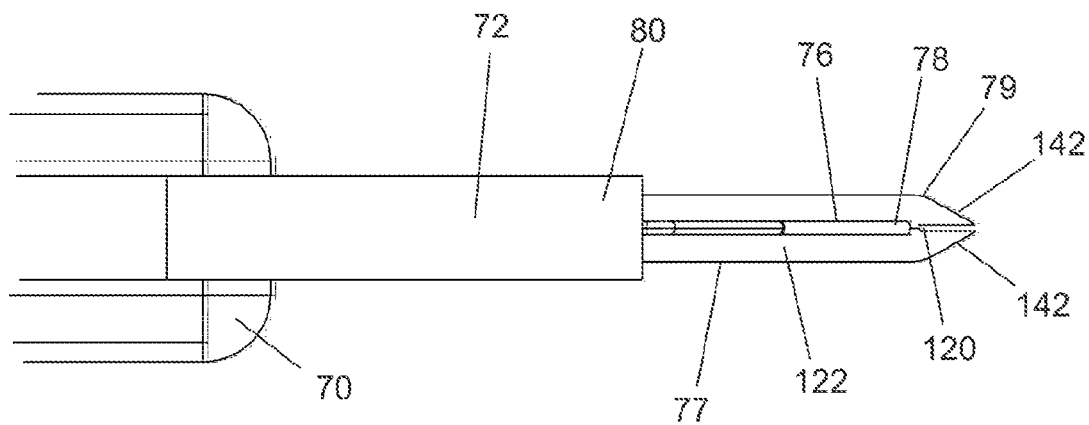
FIG. 24 is an expanded plan view of the distal portion of the distal tip assembly of another alternate embodiment.
Figure 25:
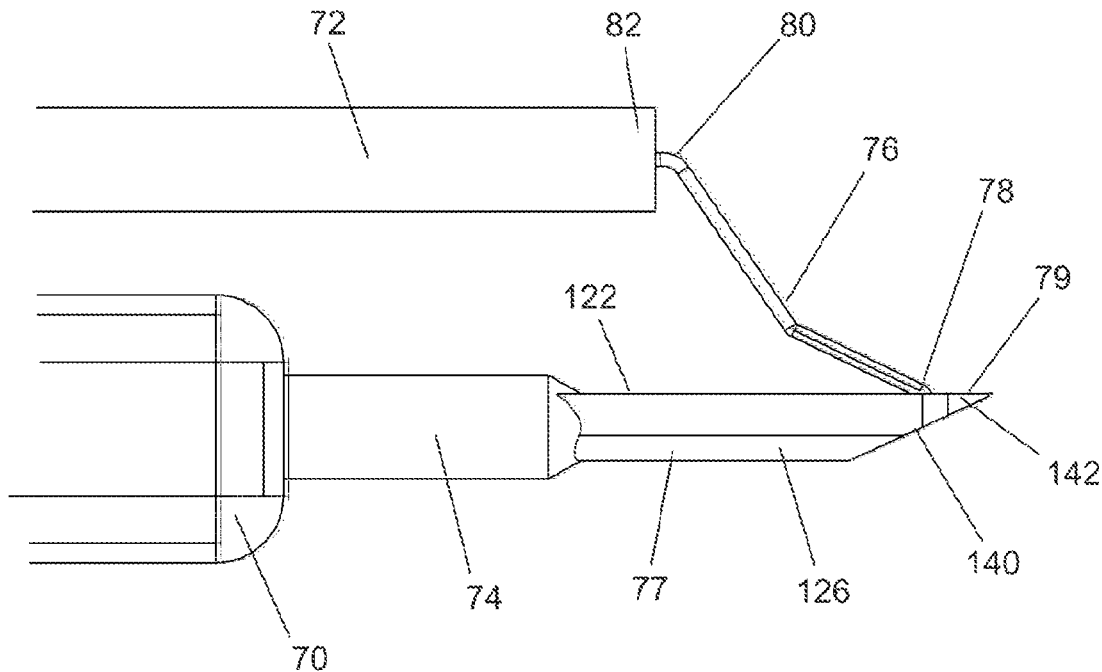
FIG. 25 is a side elevational view of the objects of FIG. 24.
Figure 26:
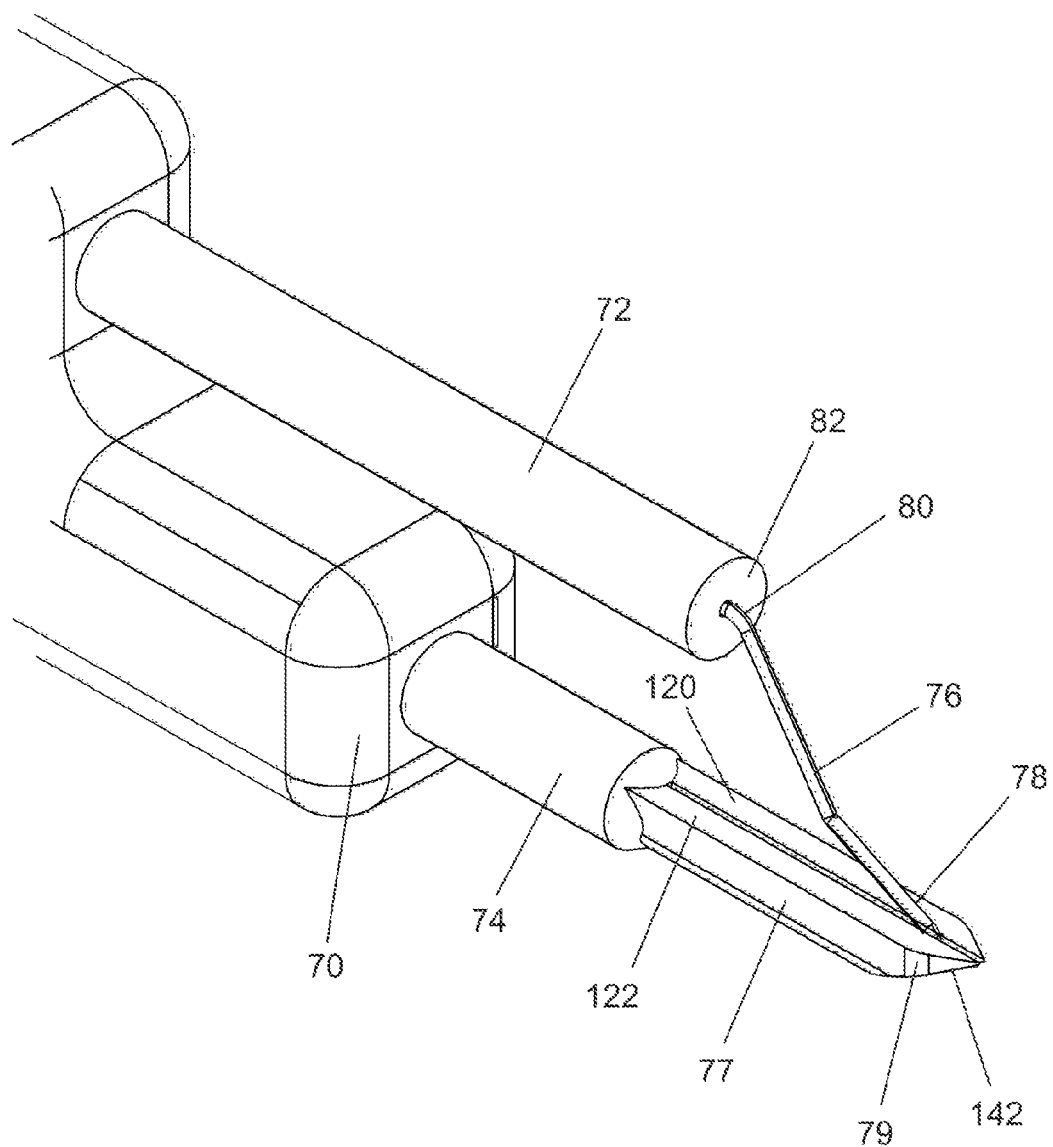
FIG. 26 is a perspective view of the objects of FIG. 24.
Figure 27:
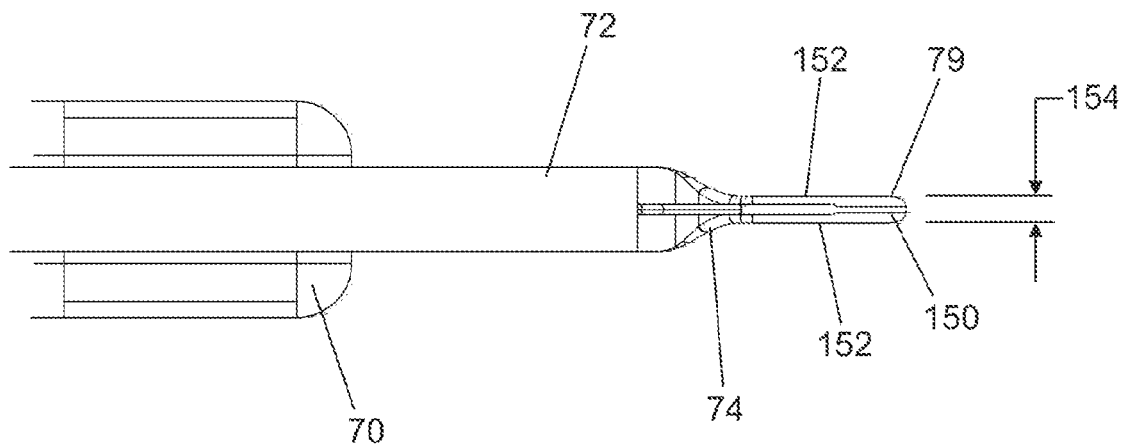
FIG. 27 is an expanded plan view of the distal portion of an alternate embodiment of the distal tip assembly of the present invention.
Figure 28:
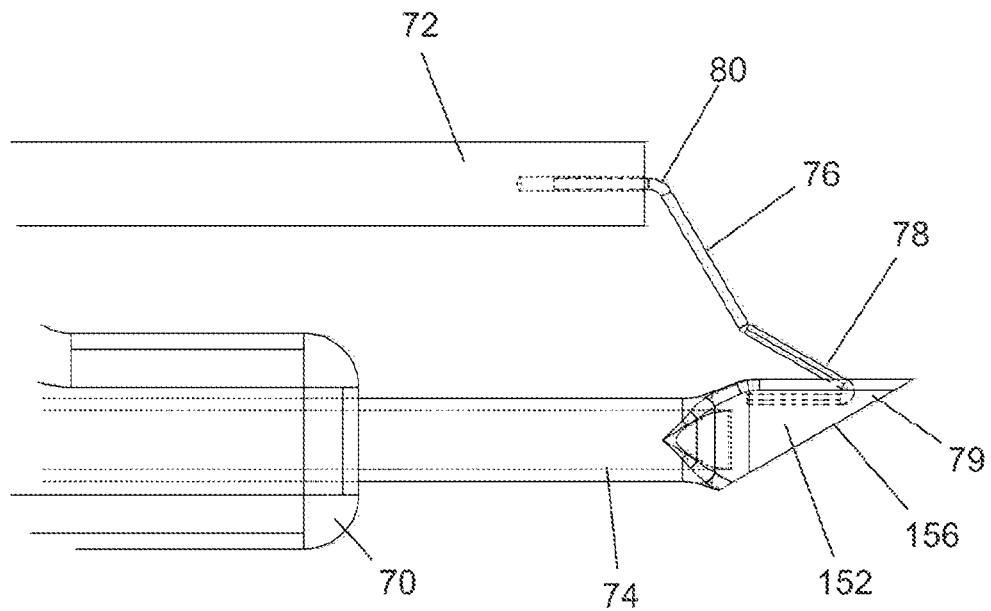
FIG. 28 is a side elevational view of the objects of FIG. 27.
Figure 29:
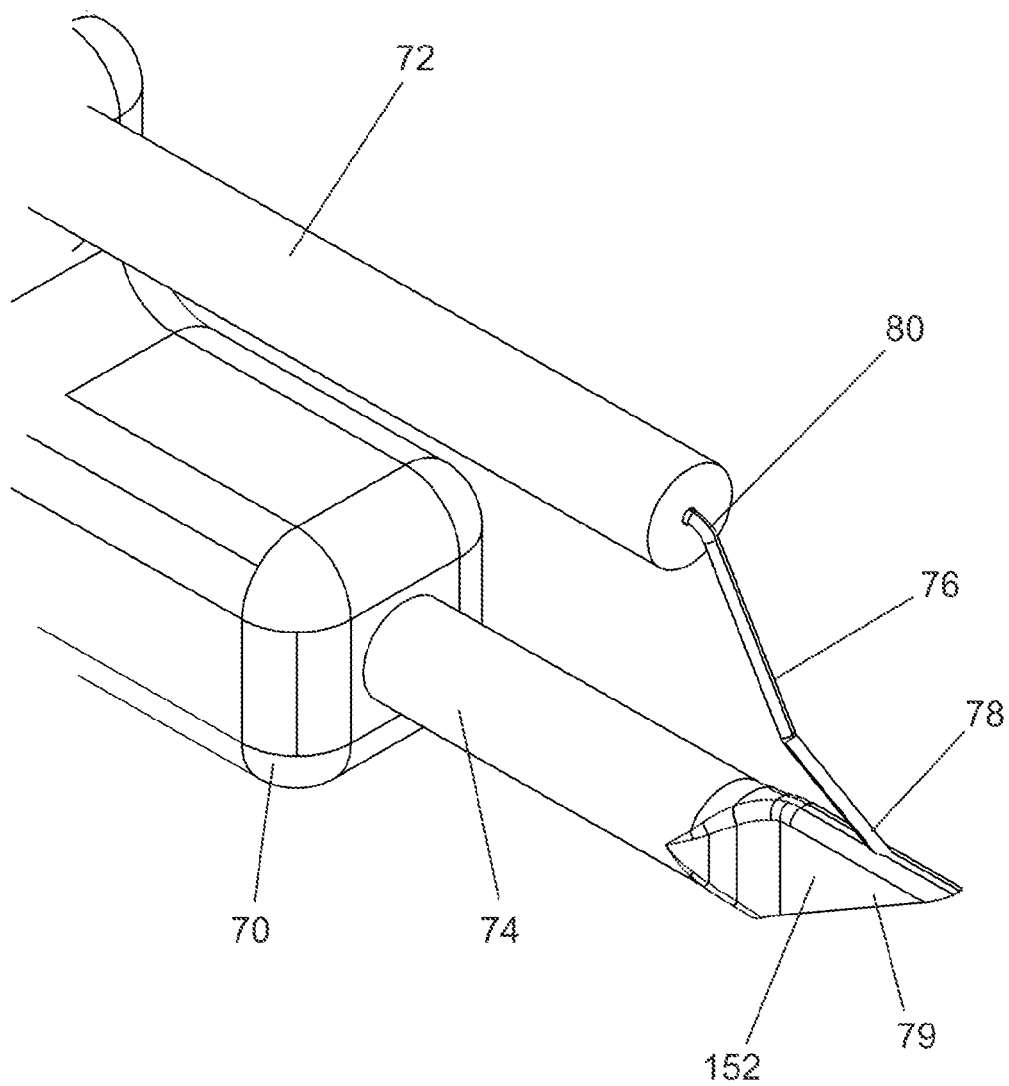
FIG. 29 is a perspective view of the objects of FIG. 27.
Figure 30:
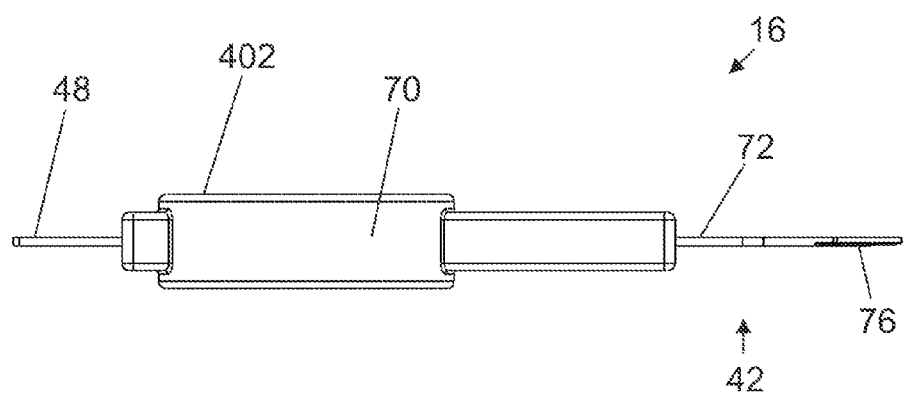
FIG. 30 is a plan view of an alternate embodiment of the distal tip assembly of the present invention

In the embodiment previously herein described, distal-most portion 79 has a more or less conical shape. Embodiments having portion 79 formed to other tapered shapes are contemplated as well. For instance, FIGS. 18 through 20 show an alternate embodiment having a distal portion 77 and distal-most portion 79 formed from a sheet material folded to form seam 120 in top surface 122 of first conductive member 74, distal end 78 of filament 76 being crimped in seam 120. Distal-most portion 79 is formed of angled surface 124 and cylindrical radii 126 formed by the folding process. Portion 79 has a tapered distal end 128 when viewed in plan view (FIG. 18). FIGS. 21 through 23 show a modification of the embodiment of FIGS. 18 through 20. A secondary coining or trimming operation forms tapered portion 130 having an included angle 132 when viewed in a plan view (FIG. 21). Referring now to FIGS. 24 through 26 showing yet another embodiment, distal-most portion 79 of first conductive piece 74 is formed from a sheet material folded to form seam 120 in top surface 122 of first conductive member 74, distal end 78 of filament 76 being crimped in seam 120. Distal-most portion 79 is formed by angled or beveled surface 140 best seen in FIG. 25, and angled surfaces 142 best seen in FIG. 24. In yet another embodiment, shown in FIGS. 27 through 29, first conductive member 74 has a tubular construction, distal end 78 of filament 76 being positioned in a slot 150 in the upper distal portion of member 74 before the end of the member is crimped to form a pair of laterally opposed, parallel planar surfaces 152 spaced distance 154 apart. Beveled surface 156 forms a wedge shape at distal-most portion 79 of member 74, Distal-most portion 79, because of its wedge shape and narrow width 154, slips easily into the loop of a suture, even one of a small size.

Referring now to FIGS. 30 through 36, which depict an alternate embodiment of the distal tip assembly, distal tip assembly 16 has a body 70 made of a suitable dielectric material. Body 70 has an enlarged portion 402 to aid in gripping assembly 16 for example, when mounting or dismounting assembly 16 from handle 12. In a preferred embodiment, body 70 is made of a polymeric material. First connector piece 46 forms the proximal end of first conductive piece 74; second connector piece 48 forms the proximal end of second conductive piece 72. These proximal connector pieces are constructed to be received within the electrical connectors (receiving sockets), 30 and 31, disposed on the distal-most surface of handle portion, 12, so as to allow for demountable connection between the elongated handle portion and distal tip assembly. As depicted herein, the connectors have a generally flat, spade-shaped proximal end; however, they may be provided with a round cross-section like those in previously described embodiments.

In a preferred embodiment, body 70 is molded around conductive pieces 72 and 74. Conductive pieces 72 and 74 are preferably formed from a sheet material of thickness 404. In a preferred embodiment, the thickness 404 ranges from 0.016 and 0.080 inches, more preferably between 0.018 and 0.060 inches. In a preferred embodiment The distal end 77 of first conductive piece 74 and distal end 82 of second conductive piece 72 each have a reduced thickness 406. In a preferred embodiment, conductive pieces 72 and 74 are formed from a stainless steel sheet by die cutting (stamping), laser cutting, wire Electrical Discharge Machining (wire EDM) or a similar through-cutting process.

Figure 31:
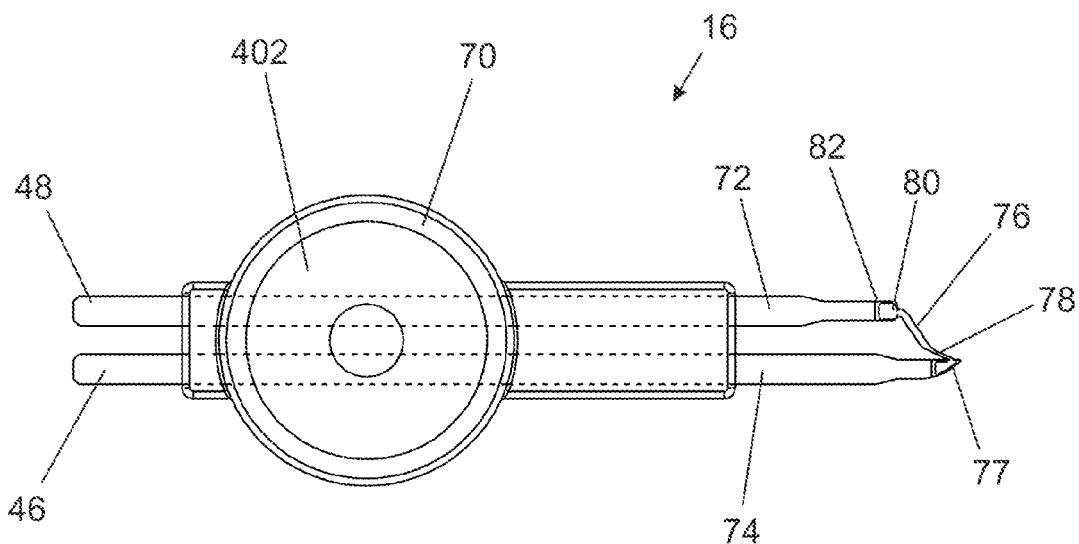
FIG. 31 is a side elevational view of the objects of FIG. 30.
Figure 32:
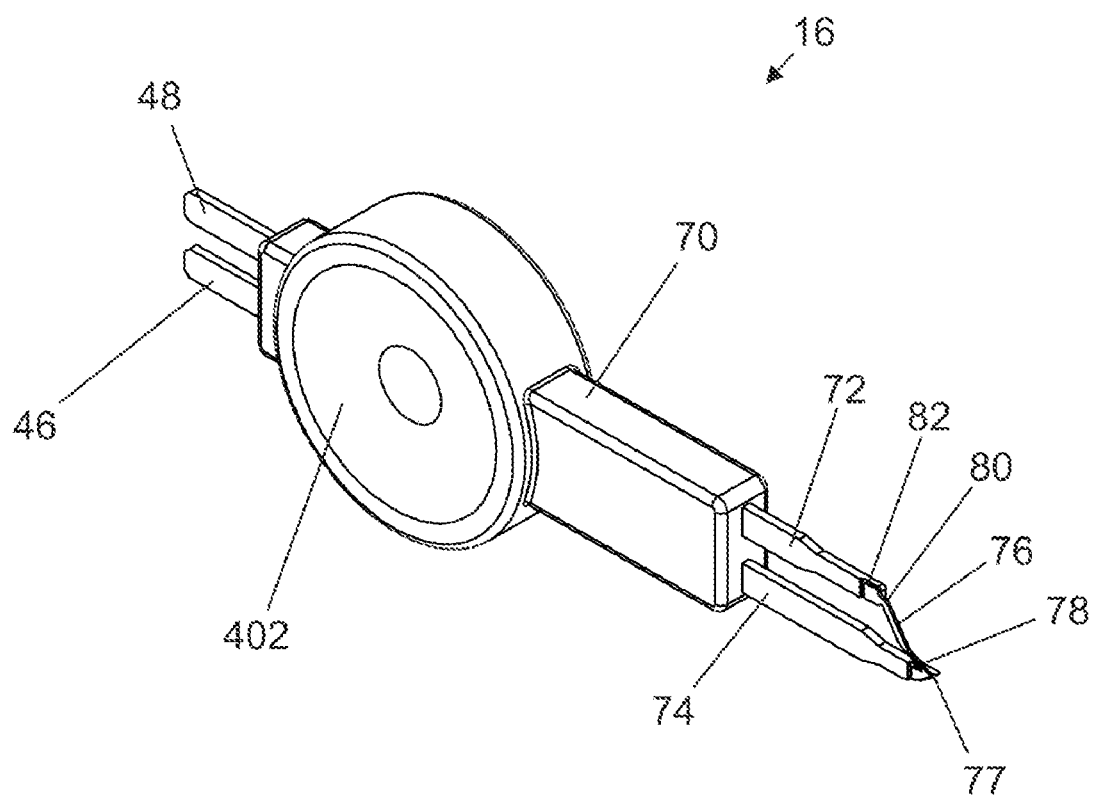
FIG. 32 is a perspective view of the objects of FIG. 30.
Figure 33:
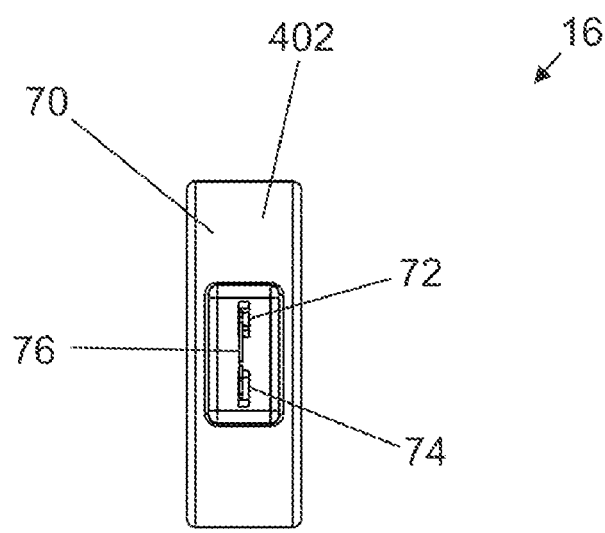
FIG. 33 is a distal end view of the objects of FIG. 30.
Figure 34:
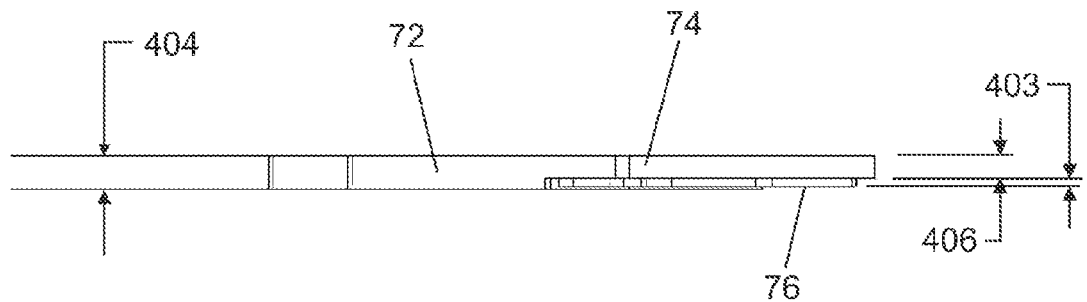
FIG. 34 is an expanded plan view of the distal portion of the objects of FIG. 30.
Figure 35:
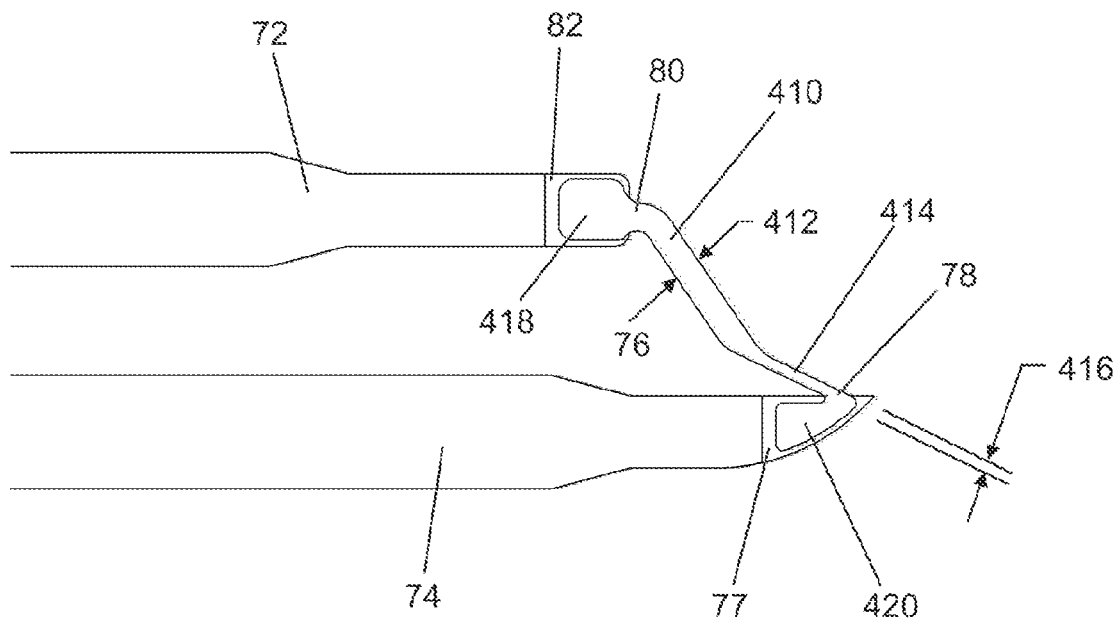
FIG. 35 is a side elevational view of the objects of FIG. 34.
Figure 36:
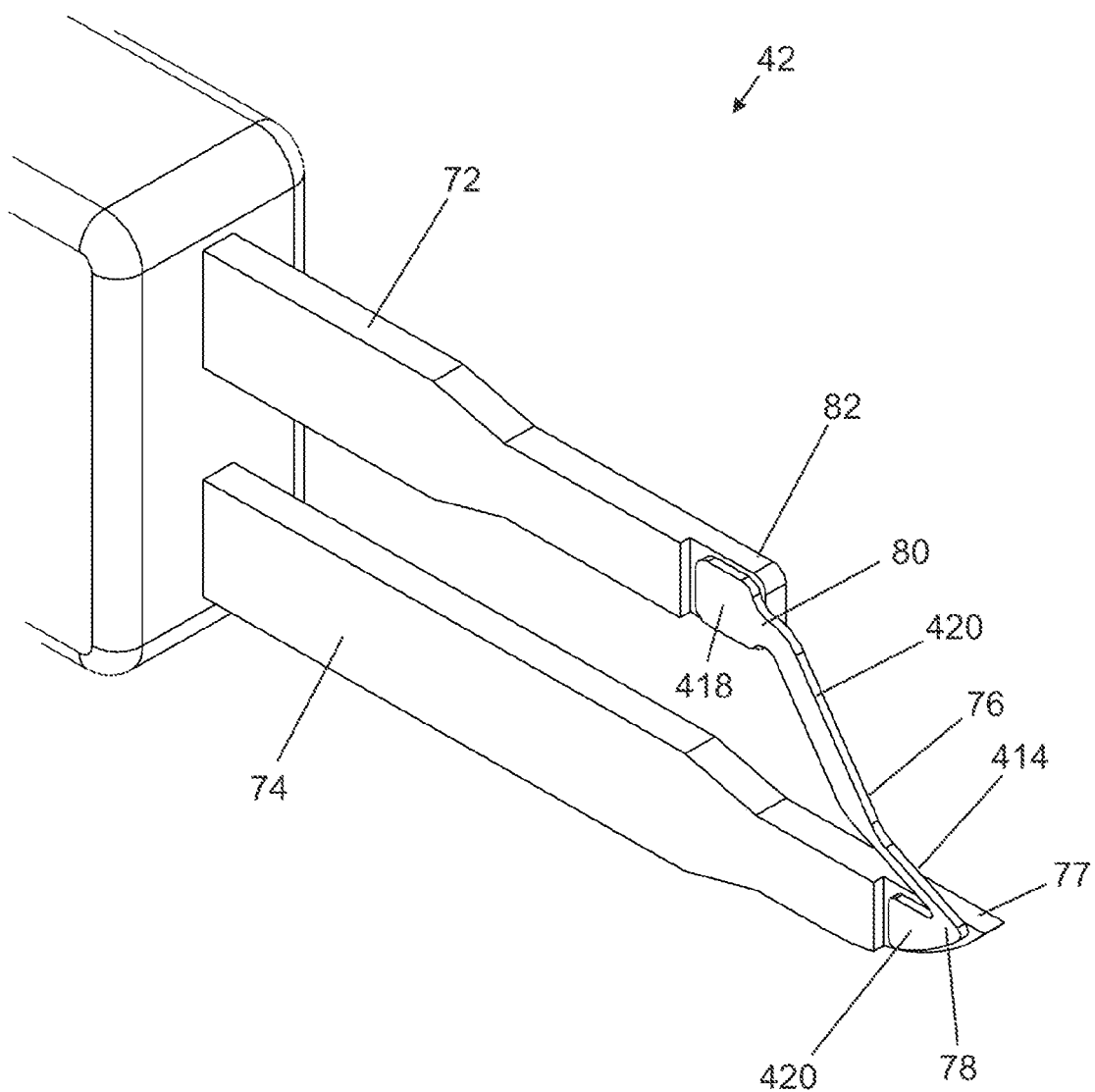
FIG. 36 is a perspective view of the objects of FIG. 34.

The distal end 42 of assembly 16 is generally wedge-shaped when viewed in a side elevational view, as in FIGS. 31 and 35, with the wedge being formed by the distal portion of first conductive piece 74 and heating element 76. Heating element 76, has a distal end 78 affixed to distal end 77 of first conductive piece 74. Proximal end 80 of element 76 is affixed to the distal end 82 of the second conductive piece 72. Heating element 76 is formed of a sheet material of thickness 408, thickness 408 being less than the difference between thicknesses 404 and 406. For example, thickness 408 is preferably between 0.002 and 0.020 inches, more preferably between 0.003 and 0.015 inches. In addition, heating element 76 preferably tapers along its length, from a first proximal portion 410 of width 412, to a distal portion 414 of width 416, such that width 416 is less than width 412, Furthermore, proximal end portion 418 and distal end portion 420 preferably have relatively large areas when viewed in a side elevational view, as in FIGS. 31 and 35, to aid in the attachment of element 76 to conductive pieces 72 and 74. In a preferred method, element 76 and pieces 72 and 74 are attached by resistance welding or laser welding. Also in a preferred embodiment, element 76 is formed by photochemical machining. In other embodiments, element 76 is formed by laser cutting, wire electrical discharge machining (wire EDM) or by die cutting, for example. When power is applied to filament 76 the heating of each of the portions of the heating element is inversely proportional to the cross-sectional area of those portions. Because distal portion 414 has a smaller cross-sectional area than proximal portion 410, distal portion 414 experiences more heating than proximal portion 410 during activation and, thus, reaches higher temperatures. Because element 76 and distal portion 77 of first conductive piece 74 are thin, distal portion 77 is able to easily slip under the loop of a stitch; thereby, the distal portion 414 of element 76 contacts the suture for cutting.

The temperatures of heating element 76 are determined by the voltage supplied to the element, the length of time that the voltage is supplied, and by the resistance of the element. The resistance of distal tip assembly 16 will vary due to manufacturing tolerances on the diameter and length of heating element 76, and due to variations in the attachment of the element 76 to conductive pieces 72 and 74. In some cases the resistance may also vary with repeated activations due to resistance changes in the attachments. Accordingly, a circuit within proximal portion 12 conditions the power supplied to element 76 so that element 76 is heated to a predetermined temperature even though battery voltage and element resistances vary within predetermined ranges.

Figure 37:
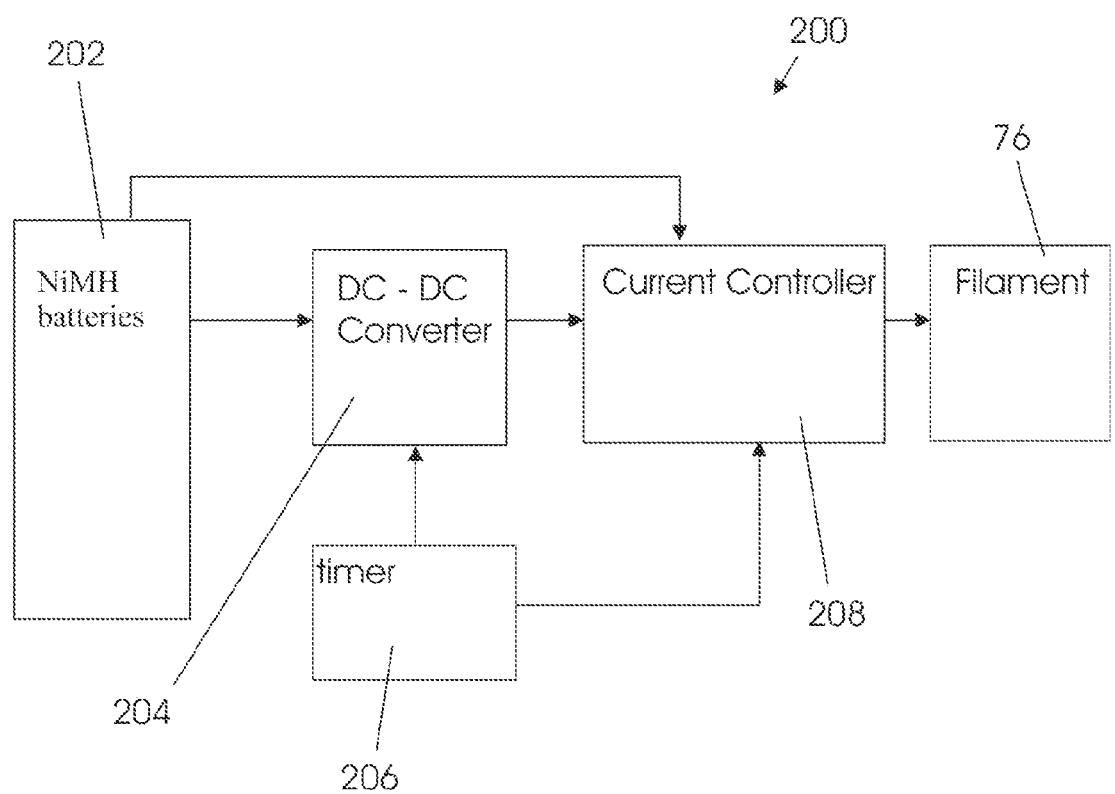
FIG. 37 is a block diagram of circuitry for controlling power supplied to the heating element.

Referring now to FIG. 37, circuit 200 for conditioning and controlling power supplied to heating element 76 has a voltage source 202, in this preferred embodiment two Nickel-Metal Hydride (NiMH) batteries, which is applied to a DC to DC voltage converter 204 which puts out voltage at a predetermined level. The output of converter 204 is supplied to timer circuit 206 and current controller 208. Current controller 208 supplies current to heating element 76 such that element 76 achieves a predetermined temperature. In a preferred embodiment current controller 208 determines the resistance of the element 76 by sensing the voltage across the element when power is supplied to the element. Current controller 208 supplies power to the element 76 until a predetermined energy value is reached, the value being the product of the voltage, current and time. Because the electrical energy is converted to thermal energy by heating element 76, the heating of element 76 is repeatable even though the resistance of the element may vary. In another embodiment current controller 208 varies the voltage supplied to element 76 based on the resistance of element 76 so as to supply a predetermined amount of energy. In yet another embodiment, used with heating elements 76 in which the resistance is closely controlled, power at a predetermined voltage is supplied to element 76 for a predetermined length of time.

When filament 76 has been energized, timer 206 prevents a second activation for a predetermined time period so as to allow heat from element 76 to dissipate in conductive pieces 72 and 74, and for conductive piece 74 to cool so that subsequent activation of the device does not cause the temperature of distal end 77 of piece 74 to rise to a level which would cause patient discomfort or harm.

Figure 38:
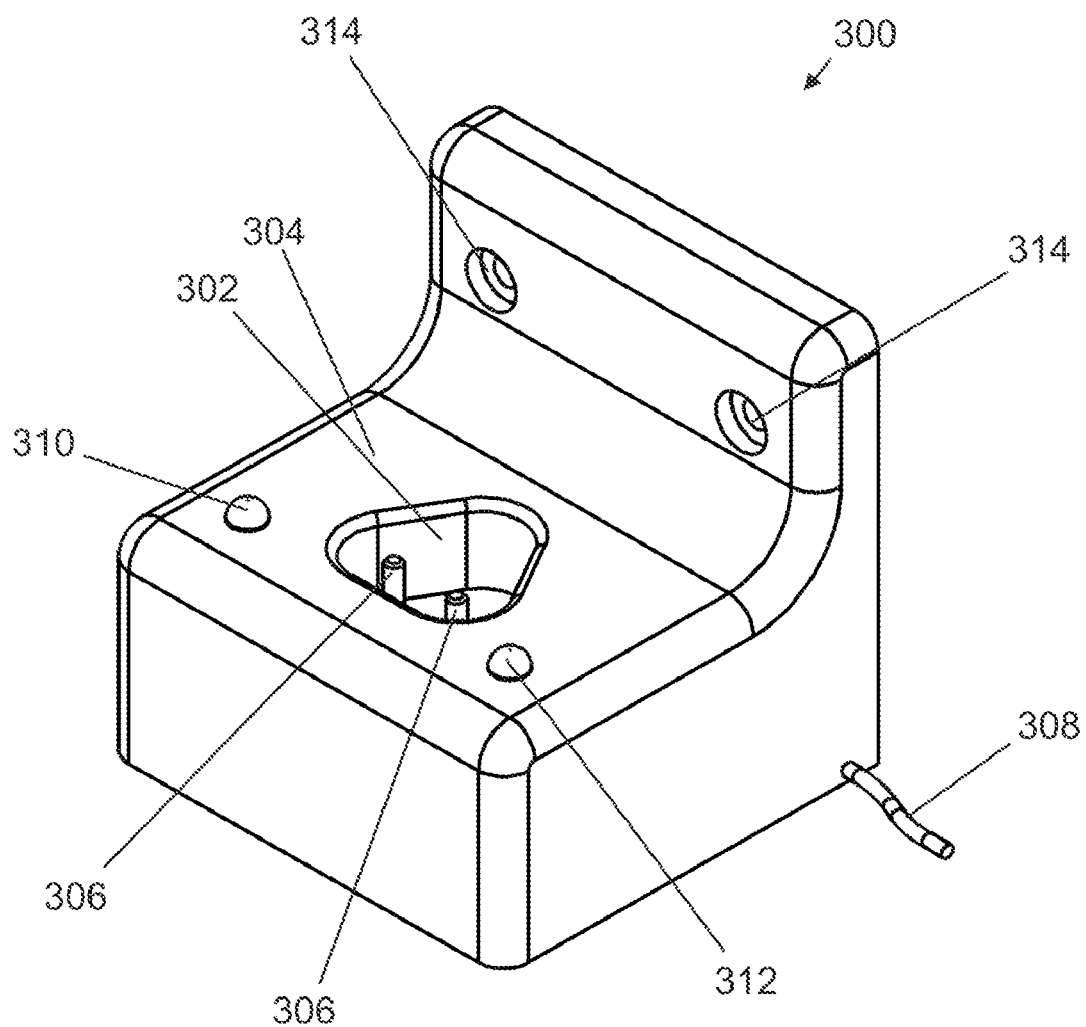
FIG. 38 is a perspective view of a charging cradle for recharging the power source of a preferred embodiment.
Figure 39:
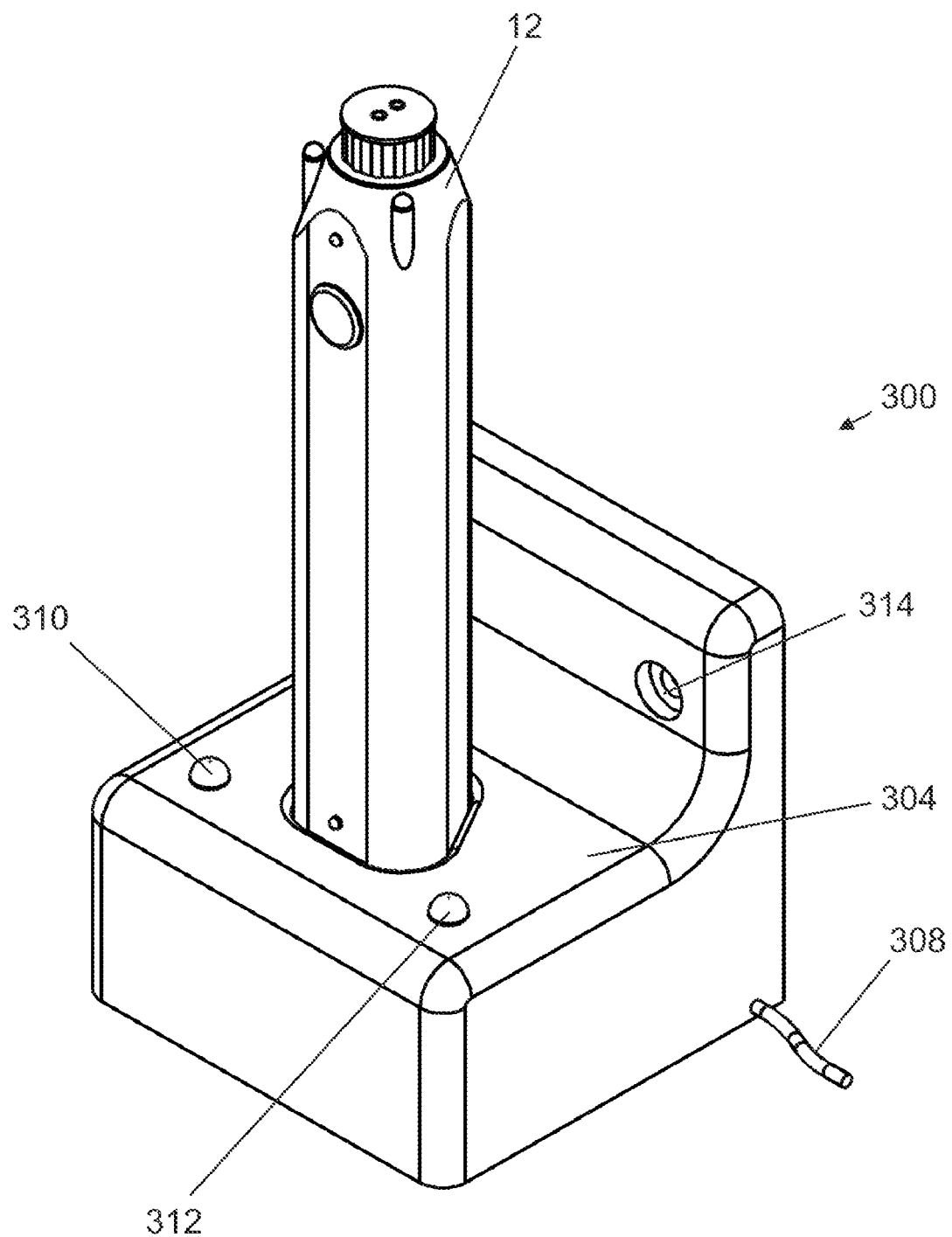
FIG. 39 is a perspective view of the charging cradle of FIG. 31 in use.

An exemplary charging cradle for recharging the batteries within handle 12 is shown in FIG. 38. Charging cradle 300 has a pocket 302 formed in surface 304, pocket 302 being shaped to receive and position proximal end 50 of handle 12 therein such that pins 306 are received by connectors 54 making an electrical connection thereto. Electrical cable 308 connects to an external voltage source. By means conventional in the art, charging cradle 300 supplies voltage to handle 12 so as to charge batteries therein. First indicator light 310 illuminates to indicate that charger 300 is connected to a power source. Second indicator light 312, when handle 12 is positioned in pocket 302 (see FIG. 39), indicates the condition of the batteries in handle 12, light 312 having a first condition when the batteries are not fully charged, and a second condition when the batteries are fully charged. Charging cradle 300 may be placed on a horizontal surface such as a table top, or mounted to a wall using fasteners placed in holes 314. In another embodiment cradle 300 supplies power to handle 12 electromagnetically so that pins 306 and connectors 54 of handle 12 are not required. In yet another embodiment, handle 12 has a removable battery pack which is placed in charging cradle 300 for recharging.

Thermal suture cutter 10 consisting of handle 12, single-use distal tip assemblies and optional magnifier assembly, together with charging cradle 300 form a system for cutting sutures for removal. Components may be sold separately or as a kit, the kit containing all elements required for suture cutting, including a plurality of distal assemblies 16.

The disclosure of each publication, patent or patent application mentioned in this specification is specifically incorporated by reference herein in its entirety.

The invention has been illustrated by reference to specific examples and preferred embodiments. However, it should be understood that the invention is intended not to be limited by the foregoing description, but to be defined by the appended claims and their equivalents.

What is claimed is:

1. A suture removal instrument comprising:
   (a) an elongated body comprising a proximal handle portion and distal portion configured to receive an insulated distal tip assembly;
   (b) a demountable insulated distal tip assembly having a generally wedge-shaped distal end, comprising (i) a first conductive member terminating in a tapered distal tip and (ii) a resistive heating element extending alongside said first conductive member and affixed at its distal end to the distal end of said tapered distal tip;
   (c) conduction means for supplying power to said heating element;
   (d) activation means for initiating an automated current control means; and
   (e) an automated current control means programmed to monitor and control the delivery of a predetermined amount of energy to the heating element as a pulse of high current having a predetermined duration, said duration ranging from 0.1 to 1 second, wherein said high current pulse of predetermined duration and energy heats said heating element to a temperature sufficient to rupture a suture but insufficient to heat said conductive member to a temperature which could potentially burn a patient.

2. The suture removal instrument of claim 1, wherein said elongated body comprises a cylindrical housing.

3. The suture removal instrument of claim 1 further comprising a magnifier assembly comprising a hinged magnifying lens detachably mounted to the distal end of said elongated body.

4. The suture removal instrument of claim 3, wherein the magnifier assembly is mounted to the elongated body by means of a friction fit.

5. The suture removal instrument of claim 3, wherein the magnifier assembly is mechanically fastened to the elongated body by means selected from the group consisting of screws, clips, mating ribs and grooves, and mating protrusions and sockets.

6. The suture removal instrument of claim 5, wherein the distal end of said elongated body comprises a cylindrical portion having a plurality of axial ribs and a distal ridge having a diameter slightly larger than said cylindrical portion, further wherein said magnifier assembly comprises a mounting ring having a plurality of axial grooves complementary to said axial ribs, whereby said mounting ring allows said magnifier assembly to be lockingly attached to the distal end of said elongated body through the engagement of said axial grooves and axial ribs.

7. The suture removal instrument of claim 1, wherein said resistive heating element comprises a thin filament.

8. The suture removal instrument of claim 7, wherein said thin filament tapers along its length from a proximal portion and a distal portion, wherein the distal portion has a smaller cross-sectional area than the proximal portion and thus is preferentially heated during activation.

9. The suture removal instrument of claim 1, wherein the cross-section of the first conductive member is significantly greater than the cross-section of the resistive heating element, such that said resistive heating element is heated to a greater extent than said first conductive member when power is applied thereto.

10. The suture removal instrument of claim 1, wherein said resistive heating element is formed from a material selected from the group consisting of nichrome, tungsten, nickel, and stainless steel.

11. The suture removal instrument of claim 1, wherein said resistive heating element forms an acute angle with the axis of said first conductive member.

12. The suture removal instrument of claim 11, wherein said acute angle ranges from about 5 to about 40 degrees.

13. The suture removal instrument of claim 1, wherein said tapered tip comprises a conical point.

14. The suture removal instrument of claim 1, wherein said tapered tip comprises a flat scoop.

15. The suture removal instrument of claim 1, wherein the distal portion of said first conductive member is formed from a sheet material folded to form a seam, further wherein the distal end of said resistive heating element is crimped into said seam.

16. The suture removal instrument of claim 1, wherein said demountable distal tip assembly further comprises first and second conductive members that are substantially straight long their respective longitudinal axes, said second conductive member extending from the insulated distal portion of said elongated body, wherein said resistive heating element is affixed at its proximal end to the distal end of said second conductive member and at its distal end to said wedge-shaped distal tip of said first conductive member.

17. The suture removal instrument of claim 16 wherein said resistive heating element is linear along its length, between said first and second conductive members, said resistive heating element forming an acute angle with the longitudinal axis of said first conductive member.

18. The suture removal instrument of claim 16 wherein said resistive heating element is bent along its length, between said first and second conductive members.

19. The suture removal instrument of claim 16 wherein said resistive heating element is curvilinear along its length, between said first and second conductive members.

20. The suture removal instrument of claim 16, wherein said first and second conductive members comprise a pair of elongated cylinders that are substantially parallel along their respective longitudinal axes.

21. The suture removal instrument of claim 20, wherein the distal ends of said first and second conductive members have a reduced cross-sectional area.

22. The suture removal instrument of claim 16 wherein the proximal end of said distal tip assembly comprises a pair of elongate connector pieces, said first connector piece forming the proximal end of said first conductive member and said second connector piece forming the proximal end of said second conductive member, further wherein the distal end of said elongated body is provided with a pair of connector sockets for receiving said connector pieces.

23. The suture removal instrument of claim 1, wherein the distal portion of said elongated body further comprises a distally projecting light assembly for illuminating the operative field.

24. The suture removal instrument of claim 23, wherein said the light assembly comprises a pair of laterally opposed light units mounted on the side of the distal portion of the handle assembly.

25. The suture removal instrument of claim 24, wherein said light units comprise light emitting diodes (LEDs) or incandescent lamps.

26. The suture removal instrument of claim 1, wherein said elongated body further comprises one or more indicator lamps for indicating battery status or activation status.

27. The suture removal instrument of claim 26, wherein said indicator lamps comprise light emitting diodes (LEDs) or incandescent lamps.

28. The suture removal instrument of claim 1, further comprising an alarm means, mounted in the proximal handle portion that emits an audible signal when power is delivered to the resistive heating element.

29. The suture removal instrument of claim 1, wherein said high current pulse of predetermined duration ranges from 0.1 to 0.5 seconds.

30. The suture removal instrument of claim 29, wherein the current control means further includes a means for modifying power output based on resistance of said heating element so as to achieve a predetermined energy value.

31. The suture removal instrument of claim 1, wherein the instrument further includes (f) a shut-off timing means which prevents a subsequent activation until a predetermined amount of time has elapsed following an initial activation so as to prevent heating of said conductive member to a temperature which could potentially burn a patient, said predetermined amount of time between said initial and subsequent activations ranging from 1 to 5 seconds.

32. The suture removal instrument of claim 1, wherein said instrument further comprises a power source contained within the handle portion of said elongated body.

33. The suture removal instrument of claim 32, wherein said power source comprises at least one battery.

34. The suture removal instrument of claim 33, wherein said power source comprises two nickel-metal hydride batteries.

35. The suture removal instrument of claim 34, wherein said at least one battery is rechargeable.

36. The suture removal instrument of claim 1, wherein said instrument further comprises a power cord adapted for connection to a wall outlet extending from said elongated body.

37. The suture removal instrument of claim 1, wherein said activation means for controlling the supply of power to said heating element comprises an actuator button.

38. A suture removal kit comprising:
i. an elongated body comprising a proximal handle portion and distal portion configured to receive an insulated distal tip assembly, said body housing a first, rechargeable power source; a conduction means for delivering power from said first power source to a heating element; an activation means for initiating an automated current control means; and an automated current control means programmed to monitor and control the delivery of a predetermined amount of energy to the heating element as a pulse of high current having a predetermined duration, said duration ranging from 0.1 to 1 second, wherein said high current pulse of predetermined duration and energy heats said heating element to a temperature sufficient to rupture a suture but insufficient to heat said conductive member to a temperature which could potentially burn a patient;
ii. one or more insulated distal tip assemblies having a generally wedge-shaped distal end, comprising (i) a first conductive member terminating in a tapered distal tip and (ii) a resistive heating element extending alongside said first conductive member and affixed at its distal end to the distal end of said tapered distal tip, said tip assembly detachably mountable to the distal end of said elongated body;
iii. a charging cradle connectable to a second, external power source for recharging the first power source housed within said elongated body.

39. The suture removal kit of claim 38, wherein the kit is provided with multiple, single use distal tip assemblies as recited in part (ii).

40. The suture removal kit of claim 38, wherein said first power source comprises at least one rechargeable battery.

41. The suture removal kit of claim 38, wherein said first power source comprises a removable battery pack and said charging cradle is configured to receive and recharge said battery pack.

42. The suture removal kit of claim 38, wherein the charging cradle is provided with a pocket shaped to receive the handle portion of said elongated body, said cradle supplying voltage from the second power source to the first power source contained within said elongated body.

43. The suture removal kit of claim 42, wherein the pocket is provided with vertically projecting pins that are received within mating connectors disposed within handle portion of said elongated body so as to provide an electrical connection therebetween.

44. The suture removal kit of claim 42, wherein the cradle electromagnetically supplies power to the first power source housed in said elongated body.

45. The suture removal kit of claim 42, wherein the cradle includes a first indicator light that indicates that charger is connected to the second power source and a second indicator light that indicates the condition of the first power source when said handle portion is received within said pocket, a first condition being when the first power source is not fully charged and a second condition being when the first power source is fully charged.

* * * * *